(12) United States Patent
Ferrera et al.

(10) Patent No.: US 8,926,680 B2
(45) Date of Patent: Jan. 6, 2015

(54) ANEURYSM NECK BRIDGING PROCESSES WITH REVASCULARIZATION SYSTEMS METHODS AND PRODUCTS THEREBY

(75) Inventors: David A. Ferrera, Redondo Beach, CA (US); John Fulkerson, Rancho Santa Margarita, CA (US)

(73) Assignee: Covidien LP, Mansfield, MA (US)

( * ) Notice: Subject to any disclaimer, the term of this patent is extended or adjusted under 35 U.S.C. 154(b) by 42 days.

(21) Appl. No.: 12/136,737

(22) Filed: Jun. 10, 2008

(65) Prior Publication Data

US 2009/0125053 A1 May 14, 2009

Related U.S. Application Data

(60) Provisional application No. 60/989,422, filed on Nov. 20, 2007, provisional application No. 61/044,392, filed on Apr. 11, 2008, provisional application No. 61/015,154, filed on Dec. 19, 2007, provisional application No. 60/987,384, filed on Nov. 12, 2007, provisional application No. 61/019,506, filed on Jan. 7, 2008.

(51) Int. Cl.
| | | |
|---|---|---|
| *A61F 2/06* | (2013.01) | |
| *A61B 17/12* | (2006.01) | |
| *A61F 2/90* | (2013.01) | |
| *A61F 2/82* | (2013.01) | |

(52) U.S. Cl.
CPC ..... *A61B 17/12022* (2013.01); *A61B 17/12118* (2013.01); *A61F 2250/0059* (2013.01); *A61B 17/1214* (2013.01); *A61F 2/90* (2013.01); *A61F 2002/823* (2013.01); *A61B 2017/1205* (2013.01)
USPC ........................................................ 623/1.11

(58) Field of Classification Search
USPC ........ 623/1.11, 1.12; 606/108, 157, 191, 192, 606/194, 198, 200
See application file for complete search history.

(56) References Cited

U.S. PATENT DOCUMENTS

| | | | |
|---|---|---|---|
| 2,709,999 | A | 6/1955 | Nagel |
| 3,174,851 | A | 3/1965 | Buehler et al. |
| 3,351,463 | A | 11/1967 | Rozner et al. |
| 3,506,171 | A | 4/1970 | Rupert |
| 3,753,700 | A | 8/1973 | Harrison et al. |

(Continued)

FOREIGN PATENT DOCUMENTS

| | | |
|---|---|---|
| EP | 0321912 | 12/1988 |
| EP | 820729 A1 | 1/1998 |

(Continued)

OTHER PUBLICATIONS

Micro Therapeutics, Inc., DBA EV3 Neurovascular, Inc., Solitaire FR Revascularization Device, Instructions for Use, 70494-001 Rev. 03/09.

(Continued)

*Primary Examiner* — Katherine M Shi
(74) *Attorney, Agent, or Firm* — Mark J. Kertz, Esq.

(57) ABSTRACT

Devices, methods and systems facilitate and enable vessel wall treatment, particularly at the neck of an aneurysm. A tethered cage-like structure functions in conjunction with supplemental therapies such as a vaso-occlusive coil delivering microcatheter system and/or pharmaceutical delivery, among other things, by stabilizing vessel walls and providing tethered cage-like therapeutic support for treating aneurysms, temporarily or on an implantable basis.

22 Claims, 32 Drawing Sheets

(56) References Cited

U.S. PATENT DOCUMENTS

| | | |
|---|---|---|
| 4,650,466 A | 3/1987 | Luther |
| 4,993,481 A | 2/1991 | Kamimoto et al. |
| 4,998,539 A | 3/1991 | Delsanti |
| 5,035,686 A | 7/1991 | Crittenden et al. |
| 5,057,114 A | 10/1991 | Wittich et al. |
| 5,222,964 A | 6/1993 | Cooper |
| 5,222,971 A | 6/1993 | Willard et al. |
| 5,275,622 A | 1/1994 | Lazarus et al. |
| 5,312,344 A | 5/1994 | Grinfeld et al. |
| 5,327,885 A | 7/1994 | Griffith |
| 5,344,395 A | 9/1994 | Whalen et al. |
| 5,370,653 A | 12/1994 | Cragg |
| 5,425,739 A | 6/1995 | Jessen |
| 5,449,372 A | 9/1995 | Schmaltz |
| 5,456,667 A | 10/1995 | Ham et al. |
| 5,527,282 A | 6/1996 | Segal |
| 5,643,309 A | 7/1997 | Myler et al. |
| 5,649,906 A | 7/1997 | Gory et al. |
| 5,653,743 A | 8/1997 | Martin |
| 5,681,336 A | 10/1997 | Clement et al. |
| 5,683,449 A | 11/1997 | Marcade |
| 5,695,469 A | 12/1997 | Segal |
| 5,718,724 A | 2/1998 | Goicoechea et al. |
| 5,792,157 A | 8/1998 | Mische |
| 5,795,322 A | 8/1998 | Boudewijn |
| 5,800,457 A | 9/1998 | Gelbfish |
| 5,800,519 A | 9/1998 | Sandock |
| 5,827,324 A | 10/1998 | Cassell et al. |
| 5,853,419 A | 12/1998 | Imran |
| 5,916,235 A | 6/1999 | Guglielmi |
| 5,922,019 A | 7/1999 | Hankh et al. |
| 5,928,260 A | 7/1999 | Chin |
| 5,938,671 A | 8/1999 | Katoh et al. |
| 5,938,697 A | 8/1999 | Killion et al. |
| 5,941,895 A | 8/1999 | Myler et al. |
| 5,947,995 A | 9/1999 | Samuels |
| 5,951,599 A | 9/1999 | McCrory |
| 5,961,547 A | 10/1999 | Razavi |
| 5,968,013 A | 10/1999 | Smith et al. |
| 5,972,016 A | 10/1999 | Morales |
| 5,972,019 A | 10/1999 | Engelson |
| 5,972,219 A | 10/1999 | Habets |
| 5,976,120 A | 11/1999 | Chow et al. |
| 5,980,514 A | 11/1999 | Kupiecki et al. |
| 6,001,118 A | 12/1999 | Daniel et al. |
| 6,010,449 A | 1/2000 | Selmon et al. |
| 6,010,498 A | 1/2000 | Guglielmi |
| 6,010,521 A | 1/2000 | Lee et al. |
| 6,015,424 A | 1/2000 | Rosenbluth et al. |
| 6,039,721 A | 3/2000 | Johnson et al. |
| 6,051,020 A | 4/2000 | Goicoechea et al. |
| 6,063,070 A | 5/2000 | Eder |
| 6,063,104 A | 5/2000 | Villar et al. |
| 6,063,111 A | 5/2000 | Hieshima et al. |
| 6,066,149 A | 5/2000 | Samson et al. |
| 6,066,158 A | 5/2000 | Engelson |
| 6,093,199 A | 7/2000 | Brown et al. |
| 6,096,034 A | 8/2000 | Kupiecki et al. |
| 6,106,548 A | 8/2000 | Roubin et al. |
| 6,117,167 A | 9/2000 | Goicoechea et al. |
| 6,123,115 A | 9/2000 | Greenhalgh |
| 6,136,006 A | 10/2000 | Johnson et al. |
| 6,146,396 A | 11/2000 | Konya et al. |
| 6,159,238 A | 12/2000 | Killion et al. |
| 6,159,239 A | 12/2000 | Greenhalgh |
| 6,164,339 A | 12/2000 | Greenhalgh |
| 6,168,592 B1 | 1/2001 | Kupiecki et al. |
| 6,168,604 B1 | 1/2001 | Cano |
| 6,190,358 B1 | 2/2001 | Fitzmaurice |
| 6,192,944 B1 | 2/2001 | Greenhalgh |
| 6,193,708 B1 | 2/2001 | Ken et al. |
| 6,210,364 B1 | 4/2001 | Anderson |
| 6,217,609 B1 | 4/2001 | Haverkost |
| 6,221,096 B1 | 4/2001 | Aiba et al. |
| 6,231,598 B1 | 5/2001 | Berry et al. |
| 6,238,430 B1 | 5/2001 | Klumb et al. |
| 6,280,413 B1 | 8/2001 | Clark et al. |
| 6,283,940 B1 | 9/2001 | Mullholland |
| 6,283,992 B1 | 9/2001 | Hankh et al. |
| 6,290,720 B1 | 9/2001 | Khosravi et al. |
| 6,302,906 B1 | 10/2001 | Goicoechea et al. |
| 6,305,436 B1 | 10/2001 | Andersen et al. |
| 6,306,141 B1 | 10/2001 | Jervis |
| 6,322,585 B1 | 11/2001 | Khosravi et al. |
| 6,325,815 B1 | 12/2001 | Kusleika et al. |
| 6,325,820 B1 | 12/2001 | Khosravi et al. |
| 6,325,822 B1 | 12/2001 | Chouinard et al. |
| 6,344,041 B1 | 2/2002 | Kupiecki et al. |
| 6,383,205 B1 | 5/2002 | Samson et al. |
| 6,390,993 B1 | 5/2002 | Cornish et al. |
| 6,402,771 B1 | 6/2002 | Palmer et al. |
| 6,454,780 B1 | 9/2002 | Wallace |
| 6,458,139 B1 | 10/2002 | Palmer et al. |
| 6,468,301 B1 | 10/2002 | Amplatz et al. |
| 6,475,236 B1 | 11/2002 | Roubin et al. |
| 6,475,237 B2 | 11/2002 | Drasler et al. |
| 6,485,500 B1 | 11/2002 | Kokish |
| 6,485,509 B2 | 11/2002 | Killion et al. |
| 6,537,294 B1 | 3/2003 | Boyle et al. |
| 6,551,341 B2 | 4/2003 | Boylan et al. |
| 6,551,342 B1 | 4/2003 | Shen et al. |
| 6,553,810 B2 | 4/2003 | Webb et al. |
| 6,554,842 B2 | 4/2003 | Heuser et al. |
| 6,554,856 B1 | 4/2003 | Doorly et al. |
| 6,558,405 B1 | 5/2003 | McInnes |
| 6,562,066 B1 | 5/2003 | Martin |
| 6,569,179 B2 | 5/2003 | Teoh et al. |
| 6,569,193 B1 | 5/2003 | Cox et al. |
| 6,575,997 B1 | 6/2003 | Palmer et al. |
| 6,589,265 B1 | 7/2003 | Palmer et al. |
| 6,592,607 B1 | 7/2003 | Palmer et al. |
| 6,592,615 B1 | 7/2003 | Marcade et al. |
| 6,605,057 B2 | 8/2003 | Fitzmaurice |
| 6,610,077 B1 | 8/2003 | Hancock et al. |
| 6,616,617 B1 | 9/2003 | Ferrera et al. |
| 6,629,953 B1 | 10/2003 | Boyd |
| 6,632,241 B1 | 10/2003 | Hancock et al. |
| 6,635,081 B2 | 10/2003 | Khosravi et al. |
| 6,638,294 B1 | 10/2003 | Palmer |
| 6,641,590 B1 | 11/2003 | Palmer et al. |
| 6,652,505 B1 | 11/2003 | Tsugita |
| 6,652,576 B1 | 11/2003 | Stalker |
| 6,660,021 B1 | 12/2003 | Palmer et al. |
| 6,663,607 B2 | 12/2003 | Slaikeu et al. |
| 6,666,829 B2 | 12/2003 | Cornish et al. |
| 6,669,723 B2 | 12/2003 | Killion et al. |
| 6,673,025 B1 | 1/2004 | Richardson et al. |
| 6,685,722 B1 | 2/2004 | Rosenbluth |
| 6,685,738 B2 | 2/2004 | Chouinard et al. |
| 6,695,813 B1 | 2/2004 | Boyle et al. |
| 6,702,843 B1 | 3/2004 | Brown et al. |
| 6,709,440 B2 | 3/2004 | Callol et al. |
| 6,716,178 B1 | 4/2004 | Kilpatrick et al. |
| 6,723,112 B2 | 4/2004 | Ho et al. |
| 6,730,104 B1 | 5/2004 | Sepetka et al. |
| 6,733,519 B2 | 5/2004 | Lashinski et al. |
| 6,746,468 B1 | 6/2004 | Sepetka et al. |
| 6,764,506 B2 | 7/2004 | Roubin et al. |
| 6,773,454 B2 | 8/2004 | Wholey et al. |
| 6,790,237 B2 | 9/2004 | Stinson |
| 6,795,979 B2 | 9/2004 | Fournier |
| 6,802,851 B2 | 10/2004 | Jones et al. |
| 6,818,015 B2 | 11/2004 | Hankh et al. |
| 6,821,291 B2 | 11/2004 | Bolea et al. |
| 6,824,558 B2 | 11/2004 | Parodi |
| 6,833,003 B2 | 12/2004 | Jones et al. |
| 6,840,958 B2 | 1/2005 | Nunez et al. |
| 6,881,220 B2 | 4/2005 | Edwin et al. |
| 6,893,413 B2 | 5/2005 | Martin |
| 6,913,612 B2 | 7/2005 | Palmer et al. |
| 6,949,620 B2 | 9/2005 | Aida et al. |
| 6,953,472 B2 | 10/2005 | Palmer et al. |
| 6,955,685 B2 | 10/2005 | Escamilla et al. |
| 6,960,227 B2 | 11/2005 | Jones et al. |

(56) References Cited

U.S. PATENT DOCUMENTS

| | | |
|---|---|---|
| 6,991,641 B2 | 1/2006 | Diaz et al. |
| 6,994,723 B1 | 2/2006 | McMahon |
| 7,001,422 B2 | 2/2006 | Escamilla et al. |
| 7,004,954 B1 | 2/2006 | Voss |
| 7,004,955 B2 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,041,116 B2 | 5/2006 | Goto et al. |
| 7,048,014 B2 | 5/2006 | Hyodoh et al. |
| 7,056,328 B2 | 6/2006 | Arnott |
| 7,056,336 B2 | 6/2006 | Armstrong et al. |
| 7,060,091 B2 | 6/2006 | Killion et al. |
| 7,089,218 B1 | 8/2006 | Visel |
| 7,112,217 B1 | 9/2006 | Kugler et al. |
| 7,118,600 B2 | 10/2006 | Dua et al. |
| 7,125,419 B2 | 10/2006 | Sequin et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,660 B2 | 12/2006 | Chobotov et al. |
| 7,156,869 B1 | 1/2007 | Pacetti |
| 7,160,317 B2 | 1/2007 | McHale |
| 7,169,165 B2 | 1/2007 | Belef et al. |
| 7,172,575 B2 | 2/2007 | El-Nounou |
| 7,172,617 B2 | 2/2007 | Colgan et al. |
| 7,175,607 B2 | 2/2007 | Lim |
| 7,179,273 B1 | 2/2007 | Palmer et al. |
| 7,179,284 B2 | 2/2007 | Khosravi et al. |
| 7,201,769 B2 | 4/2007 | Jones et al. |
| 7,201,770 B2 | 4/2007 | Johnson |
| 7,223,284 B2 | 5/2007 | Khosravi et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,147 B2 | 11/2007 | Hartley |
| 7,300,458 B2 | 11/2007 | Henkes et al. |
| 7,306,619 B1 | 12/2007 | Palmer |
| 7,309,345 B2 | 12/2007 | Wallace |
| 7,309,351 B2 | 12/2007 | Escamilla |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,550 B2 | 3/2008 | Carrison et al. |
| 7,344,556 B2 | 3/2008 | Seguin et al. |
| 7,351,255 B2 | 4/2008 | Andreas |
| 7,354,455 B2 | 4/2008 | Stinson |
| 7,402,169 B2 | 7/2008 | Killion et al. |
| 7,407,509 B2 | 8/2008 | Greenberg et al. |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,494,474 B2 | 2/2009 | Richardson et al. |
| 7,549,974 B2 | 6/2009 | Nayak |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 | 7/2010 | Phung |
| 7,780,694 B2 | 8/2010 | Palmer et al. |
| 7,833,240 B2 | 11/2010 | Okushi et al. |
| 7,972,342 B2 | 7/2011 | Gandhi et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 2001/0000797 A1 | 5/2001 | Mazzocchi |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0044633 A1* | 11/2001 | Klint ............................ 606/200 |
| 2001/0044647 A1 | 11/2001 | Pinchuk et al. |
| 2001/0047202 A1 | 11/2001 | Slaikeu et al. |
| 2001/0051823 A1 | 12/2001 | Khosravi et al. |
| 2002/0004681 A1 | 1/2002 | Teoh et al. |
| 2002/0007210 A1 | 1/2002 | Chouinard et al. |
| 2002/0016564 A1 | 2/2002 | Courtney et al. |
| 2002/0016624 A1 | 2/2002 | Patterson et al. |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | McGuckin, Jr. et al. |
| 2002/0087209 A1 | 7/2002 | Edwin et al. |
| 2002/0091355 A1 | 7/2002 | Hayden |
| 2002/0095141 A1 | 7/2002 | Belef |
| 2002/0143387 A1 | 10/2002 | Soetikno et al. |
| 2002/0161377 A1 | 10/2002 | Rabkin |
| 2002/0169458 A1 | 11/2002 | Connors, III |
| 2002/0183831 A1* | 12/2002 | Rolando et al. .............. 623/1.15 |
| 2002/0198588 A1 | 12/2002 | Armstrong et al. |
| 2003/0004536 A1 | 1/2003 | Boylan et al. |
| 2003/0023230 A1 | 1/2003 | Lewis et al. |
| 2003/0023299 A1 | 1/2003 | Amplatz et al. |
| 2003/0032941 A1 | 2/2003 | Boyle |
| 2003/0032977 A1 | 2/2003 | Brady |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0199921 A1 | 10/2003 | Palmer et al. |
| 2003/0204202 A1 | 10/2003 | Palmer et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0019322 A1 | 1/2004 | Hoffmann |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez, Jr. et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0068314 A1* | 4/2004 | Jones et al. .................. 623/1.15 |
| 2004/0073300 A1 | 4/2004 | Chouinard et al. |
| 2004/0078071 A1 | 4/2004 | Escamilla et al. |
| 2004/0079429 A1 | 4/2004 | Miller et al. |
| 2004/0088002 A1 | 5/2004 | Boyle |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0153117 A1 | 8/2004 | Clubb et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |

(56) References Cited

U.S. PATENT DOCUMENTS

| | | |
|---|---|---|
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0033334 A1 | 2/2005 | Santra et al. |
| 2005/0033349 A1 | 2/2005 | Jones et al. |
| 2005/0033409 A1 | 2/2005 | Burke et al. |
| 2005/0038447 A1 | 2/2005 | Huffmaster |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0055047 A1 | 3/2005 | Greenhalgh |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0090888 A1* | 4/2005 | Hines et al. ............ 623/1.11 |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman et al. |
| 2005/0125023 A1 | 6/2005 | Bates |
| 2005/0126979 A1 | 6/2005 | Lowe |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0177228 A1 | 8/2005 | Solem et al. |
| 2005/0187612 A1 | 8/2005 | Edwin |
| 2005/0192661 A1 | 9/2005 | Griffen et al. |
| 2005/0209673 A1 | 9/2005 | Shaked |
| 2005/0209675 A1* | 9/2005 | Ton et al. ............ 623/1.11 |
| 2005/0209678 A1 | 9/2005 | Henkes et al. |
| 2005/0216050 A1 | 9/2005 | Sepetka et al. |
| 2005/0222583 A1 | 10/2005 | Cano |
| 2005/0222607 A1 | 10/2005 | Palmer et al. |
| 2005/0267570 A1 | 12/2005 | Shadduck |
| 2005/0277978 A1 | 12/2005 | Greenhalgh |
| 2006/0020285 A1 | 1/2006 | Niermann |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson |
| 2006/0052816 A1 | 3/2006 | Bates et al. |
| 2006/0058833 A1 | 3/2006 | VanCamp |
| 2006/0058836 A1 | 3/2006 | Bose et al. |
| 2006/0058838 A1 | 3/2006 | Bose et al. |
| 2006/0074480 A1 | 4/2006 | Bales et al. |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122685 A1 | 6/2006 | Bonsignore et al. |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0195172 A1 | 8/2006 | Luo et al. |
| 2006/0200048 A1 | 9/2006 | Furst |
| 2006/0200221 A1 | 9/2006 | Malewicz |
| 2006/0224180 A1 | 10/2006 | Anderson et al. |
| 2006/0229645 A1 | 10/2006 | Bonnette et al. |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0287701 A1 | 12/2006 | Pal |
| 2006/0287704 A1 | 12/2006 | Hartley et al. |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135826 A1* | 6/2007 | Zaver et al. ............ 606/157 |
| 2007/0135888 A1 | 6/2007 | Khosravi et al. |
| 2007/0141036 A1 | 6/2007 | Gorrochategui Barrueta et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski |
| 2007/0198030 A1 | 8/2007 | Martin et al. |
| 2007/0198075 A1 | 8/2007 | Levy |
| 2007/0203452 A1 | 8/2007 | Mehta |
| 2007/0203559 A1 | 8/2007 | Freudenthal et al. |
| 2007/0208367 A1 | 9/2007 | Fiorella |
| 2007/0208371 A1 | 9/2007 | French et al. |
| 2007/0219621 A1 | 9/2007 | Hartley et al. |
| 2007/0225794 A1 | 9/2007 | Thramann et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288034 A1 | 12/2007 | MacCollum et al. |
| 2007/0288037 A1 | 12/2007 | Cheng et al. |
| 2007/0288080 A1 | 12/2007 | Maccollum et al. |
| 2007/0288083 A1 | 12/2007 | Hines |
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt |
| 2008/0058724 A1 | 3/2008 | Wallace |
| 2008/0071178 A1 | 3/2008 | Greenland et al. |
| 2008/0077175 A1 | 3/2008 | Palmer |
| 2008/0082159 A1 | 4/2008 | Tseng et al. |
| 2008/0086196 A1 | 4/2008 | Truckai et al. |
| 2008/0097495 A1 | 4/2008 | Feller, III et al. |
| 2008/0103477 A1 | 5/2008 | Jones |
| 2008/0103585 A1 | 5/2008 | Monstadt |
| 2008/0109063 A1 | 5/2008 | Hancock et al. |
| 2008/0109067 A1 | 5/2008 | Caro et al. |
| 2008/0114445 A1 | 5/2008 | Melsheimer et al. |
| 2008/0125855 A1 | 5/2008 | Henkes et al. |
| 2008/0140107 A1 | 6/2008 | Bei |
| 2008/0140181 A1 | 6/2008 | Reynolds |
| 2008/0147100 A1 | 6/2008 | Wallace |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0195140 A1 | 8/2008 | Myla |
| 2008/0200946 A1 | 8/2008 | Braun et al. |
| 2008/0208319 A1 | 8/2008 | Rabkin et al. |
| 2008/0221554 A1 | 9/2008 | O'Connor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1* | 9/2008 | Snow et al. ............ 623/1.11 |
| 2008/0243229 A1 | 10/2008 | Wallace et al. |
| 2008/0243232 A1 | 10/2008 | Hegg et al. |
| 2008/0247943 A1 | 10/2008 | Lanza et al. |
| 2008/0249598 A1 | 10/2008 | Sherry |
| 2008/0255678 A1 | 10/2008 | Cully et al. |
| 2008/0262506 A1 | 10/2008 | Griffin |
| 2008/0262528 A1 | 10/2008 | Martin |
| 2008/0262532 A1 | 10/2008 | Martin |
| 2008/0262592 A1 | 10/2008 | Jordan et al. |

(56) References Cited

U.S. PATENT DOCUMENTS

| | | |
|---|---|---|
| 2008/0262952 A1 | 10/2008 | Channell |
| 2008/0269774 A1 | 10/2008 | Garcia et al. |
| 2008/0269868 A1 | 10/2008 | Bei |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0125053 A1 | 5/2009 | Ferrera et al. |
| 2009/0192455 A1 | 7/2009 | Ferrera et al. |
| 2009/0292297 A1 | 11/2009 | Ferrera |
| 2009/0299393 A1 | 12/2009 | Martin et al. |
| 2010/0022951 A1 | 1/2010 | Ferrera et al. |
| 2010/0100106 A1 | 4/2010 | Ferrera et al. |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0299911 A1 | 12/2010 | Gianotti et al. |
| 2010/0318097 A1 | 12/2010 | Ferrera et al. |
| 2011/0009875 A1 | 1/2011 | Grandfield et al. |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0089216 A1 | 4/2012 | Rapaport et al. |
| 2012/0116443 A1 | 5/2012 | Ferrera et al. |

FOREIGN PATENT DOCUMENTS

| | | |
|---|---|---|
| EP | 1000590 | 5/2000 |
| EP | 1437097 | 7/2004 |
| EP | 2257248 | 10/2011 |
| EP | 2301450 | 11/2011 |
| EP | 2417919 | 2/2012 |
| JP | 2003-033359 A | 2/2003 |
| JP | 2006-094876 | 4/2006 |
| JP | 2007-222658 A | 9/2007 |
| JP | 2007-236471 A | 9/2007 |
| WO | WO-94/03127 A1 | 2/1994 |
| WO | WO98/55173 | 12/1998 |
| WO | WO00/32265 | 6/2000 |
| WO | WO00/53120 | 9/2000 |
| WO | WO01/08743 | 2/2001 |
| WO | WO01/36034 | 5/2001 |
| WO | WO01/45569 | 6/2001 |
| WO | WO03/011188 | 2/2003 |
| WO | WO03/017823 | 3/2003 |
| WO | WO2007/089897 | 8/2007 |
| WO | WO2007/121005 | 10/2007 |
| WO | WO2008/117256 | 10/2008 |
| WO | WO2008/117257 | 10/2008 |
| WO | WO-2008/124728 | 10/2008 |
| WO | WO2009/105710 | 8/2009 |
| WO | WO2009/124288 | 10/2009 |
| WO | WO2009/126747 | 10/2009 |
| WO | WO2010/010545 | 1/2010 |
| WO | WO2010/023671 | 3/2010 |
| WO | WO2010/046897 | 4/2010 |
| WO | WO2010/049121 | 5/2010 |
| WO | WO2010/062363 | 6/2010 |
| WO | WO2010/102307 | 9/2010 |
| WO | WO2010/115642 | 10/2010 |
| WO | WO2010/121037 | 10/2010 |
| WO | WO2010/121049 | 10/2010 |
| WO | WO2011/054531 | 5/2011 |
| WO | WO2011/095352 | 8/2011 |
| WO | WO2011/133486 | 10/2011 |
| WO | WO2011/135556 | 11/2011 |
| WO | WO2011/144336 | 11/2011 |
| WO | WO2011/147567 | 12/2011 |
| WO | WO2012/009675 | 1/2012 |
| WO | WO2012/025245 | 3/2012 |
| WO | WO2012/025247 | 3/2012 |

OTHER PUBLICATIONS

Micro Therapeutics, Inc., DBA EV3 Neurovascular, Inc., Fully deployable. Completely retrievable. Solitaire AB, Neurovascular Remodeling Device.

Robertson, Kathy, Stroke device startup lands National Science Foundation grant, Sacramento Business Journal, Oct. 23, 2009, Sacramento, California, USA.

Michael E. Kelly, MD, et al., Recanalization of an Acute Middle Cerebral Artery Occlusion Using a Self-Expanding, Reconstrainable, Intracranial Microstent as a Temporary Endovascular Bypass; Stroke, Jun. 2008, pp. 1770-1773, vol. 39, issue 6, United States.

Eric Sauvegeau, MD et al., Middle Cerebral Artery Stenting for Acute Ischemic Stroke After Unsuccessful Merci Retrieval; Neurosurgery

(56) References Cited

OTHER PUBLICATIONS (Special Technical Report), Apr. 2007, pp. 701-706, vol. 60, issue 4, United States.

David M. Pelz, et al., Advances in Interventional Neuroradiology 2007; Stroke, Jan. 2008, pp. 268-272, vol. 39, issue 1, United States.

Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion; Stroke, Aug. 2007, pp. 2270-2274, vol. 38, issue 8, United States.

E.I. Levy et al., Self-Expanding Stents for Recanalization of Acute Cerebrovascular Occlusions; AJNR, May 2007, pp. 816-822, vol. 28, United States.

International Search Report of May 27, 2009 for PCT/US2008/084245.

T.W. Duerig, D.E. Tolomeo, M. Wholey, An Overview of Superelastic Stent Design 2000.

Henkes, H. et al., "A Microcatheter-Delivered Highly-Flexible and Fully-Retrievable Stent, Specifically Designed for Intracranial Use," *Interventional Neuroradiology*, vol. 9, pp. 391-393 (Dec. 2003).

Doerfler, A. et al., "A Novel Flexible, Retrievable Endovascular Stent System for Small-Vessel Anatomy: Preliminary in Vivo Data," *Am. J. Neuroradiol.* vol. 26, pp. 862-868 (Apr. 2005).

Liebig, T. et al., "A novel self-expanding fully retrievable intracranial stent (SOLO): experience in nine procedures of stent-assisted aneurysm coil occlusion," *Neuroradiology* vol. 48, pp. 471-478 (Jul. 2006).

Yavuz, K. et al., "Immediate and midterm follow-up results of using an electrodetachable, fully retrievable SOLO stent system in the endovascular coil occlusion of wide-necked cerebral aneurysms," J. Neurosurg. vol. 107, pp. 49-55 (Jul. 2007).

"Penumbra, Inc. Enrolls First Patients in Pulse Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Enrolls-Patients-PULSE-Clinical-Trial-Evaluate.

U.S. Appl. No. 60/987,384, filed Nov. 12, 2007, Fulkerson et al.
U.S. Appl. No. 60/989,422, filed Nov. 20, 2007, Ferrera et al.
U.S. Appl. No. 61/015,154, filed Dec. 19, 2007, Ferrera et al.
U.S. Appl. No. 61/044,392, filed Apr. 11, 2008, Ferrera.

Wakhloo, et al., "Retrievable Closed Cell Intracranial Stent for Foreign Body and Clot Removal," Neurosurgery, May 2008.

\* cited by examiner

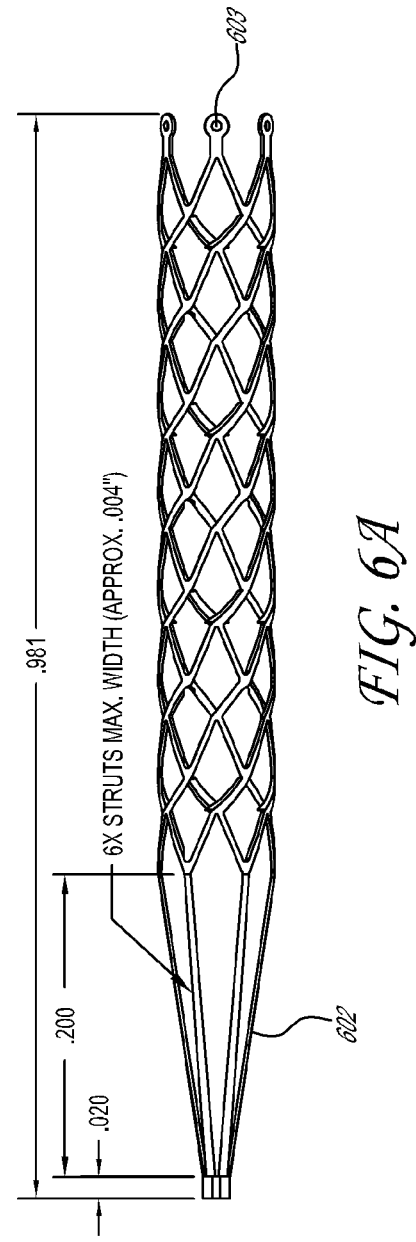
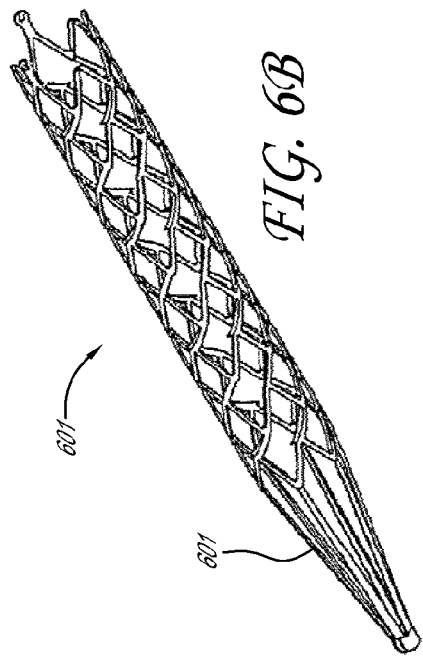
FIG. 6A
FIG. 6B

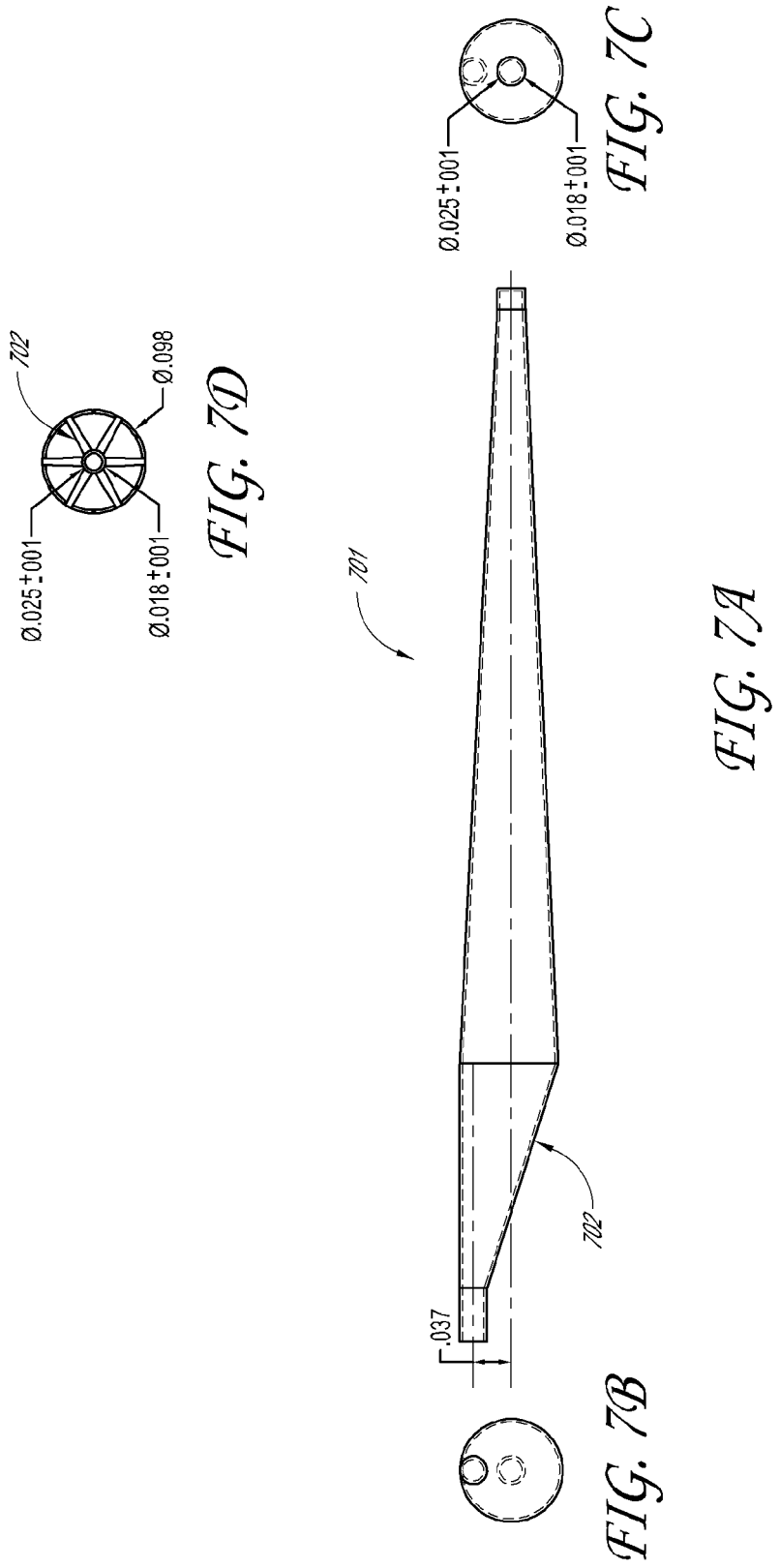

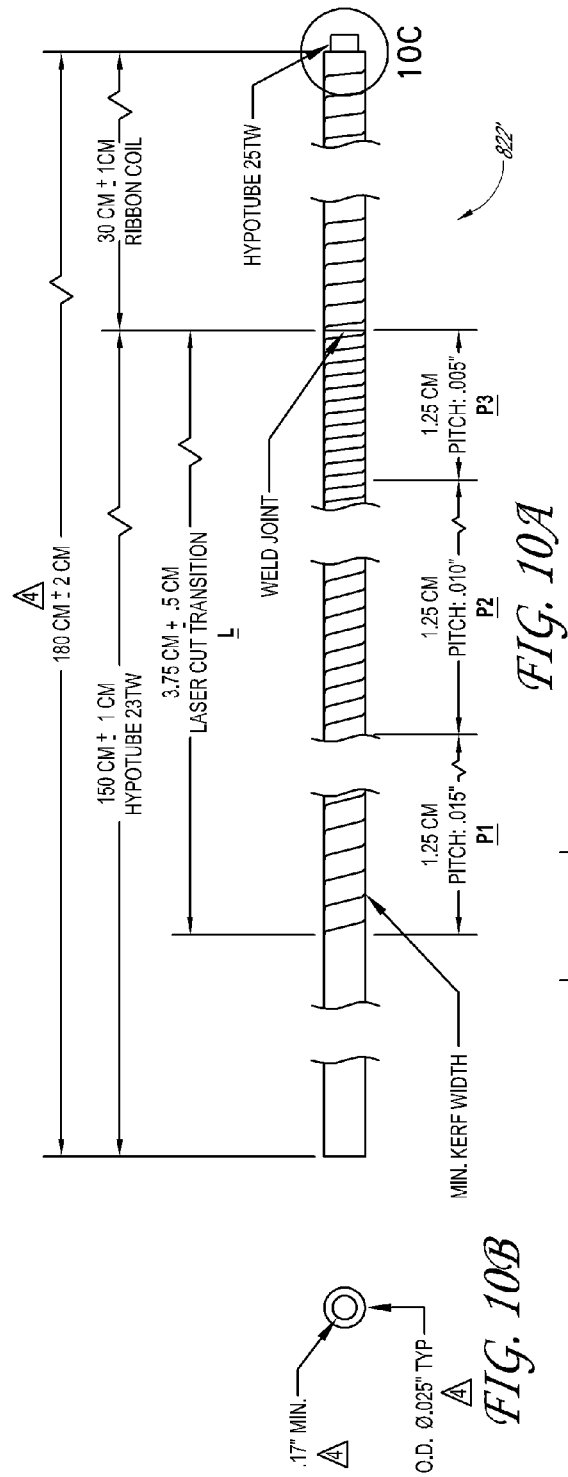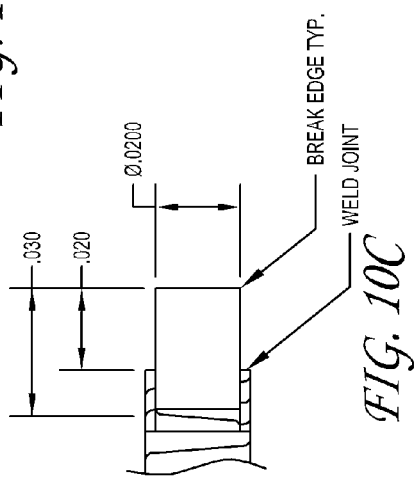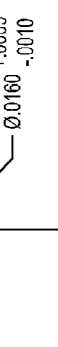
FIG. 10A
FIG. 10B
FIG. 10C
FIG. 10D

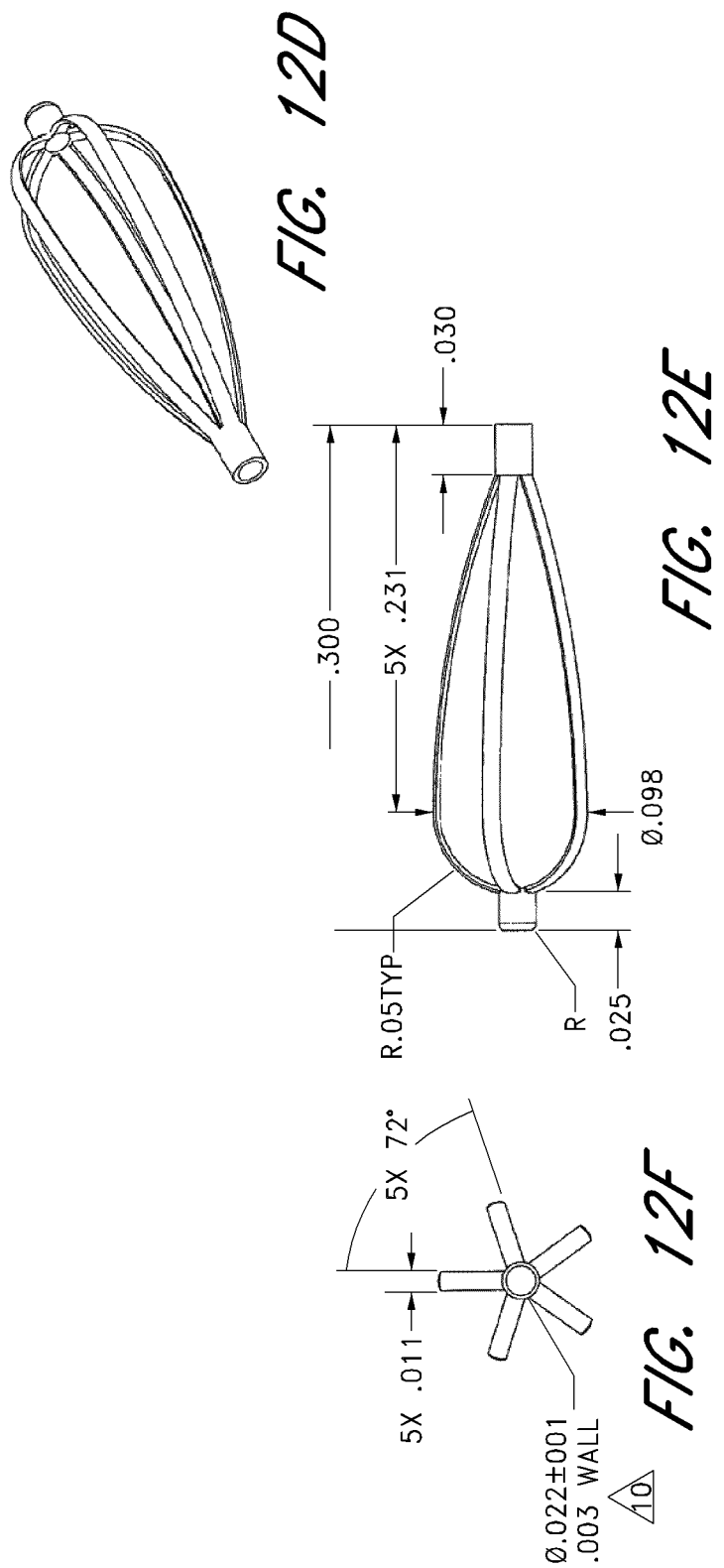

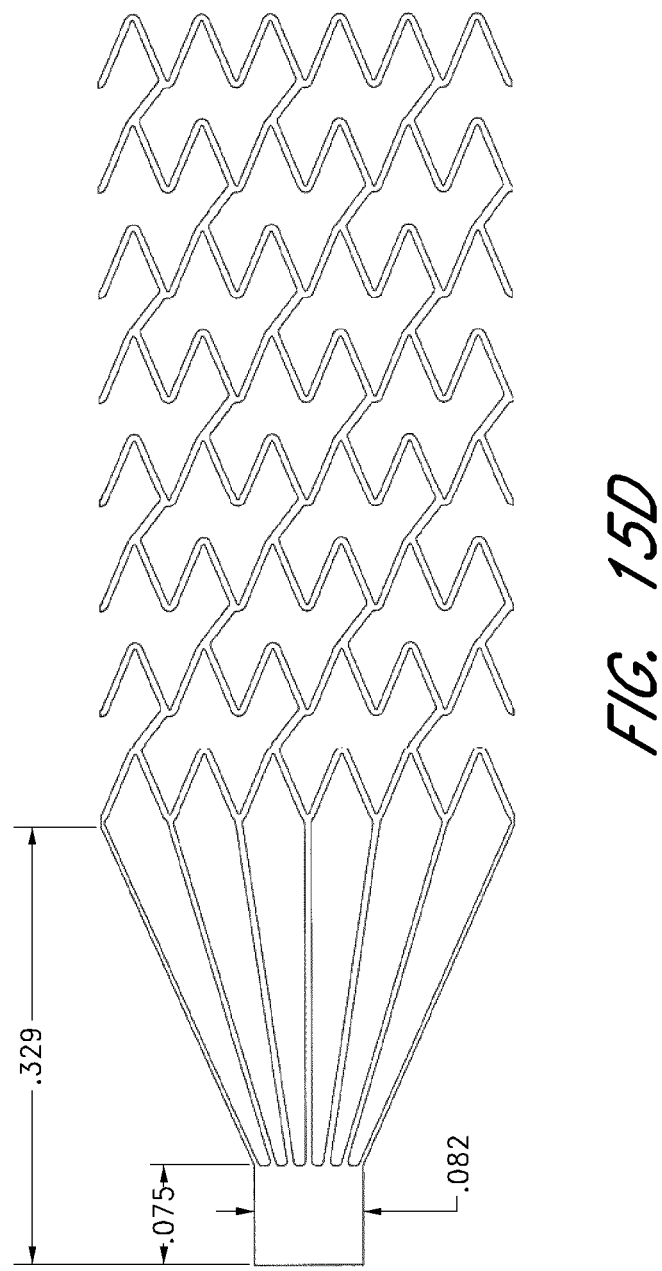

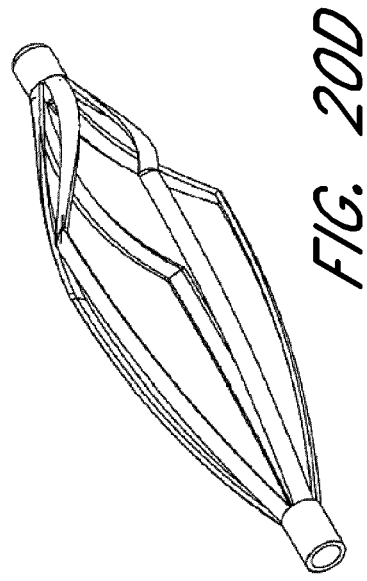
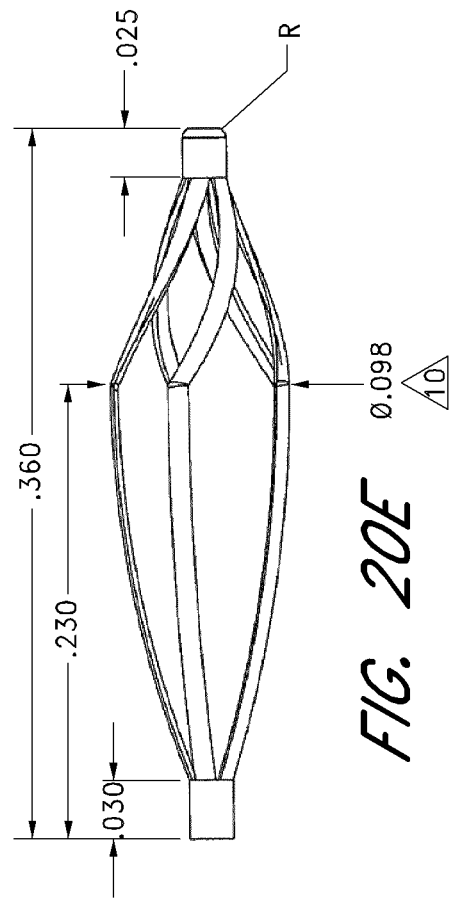
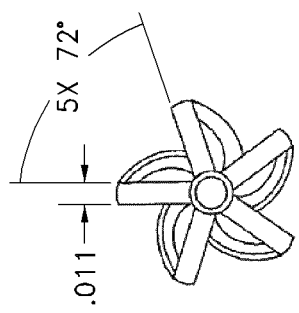
FIG. 20D
FIG. 20E
FIG. 20F

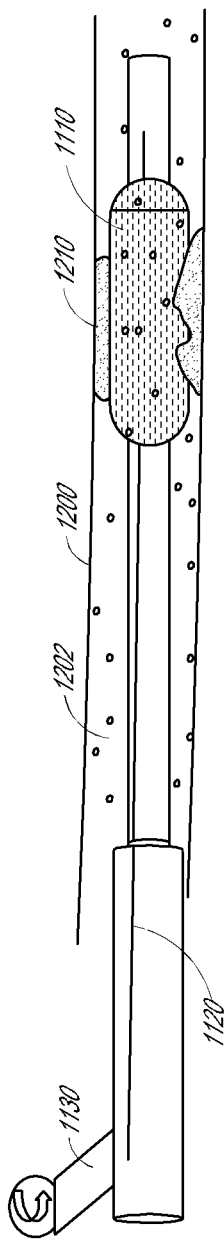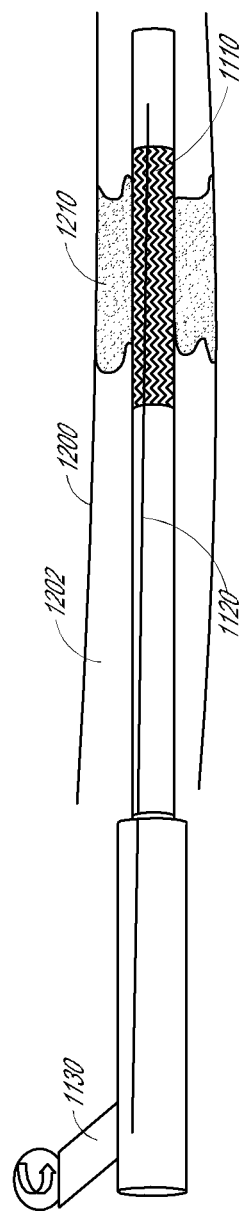
FIG. 22A
FIG. 22B

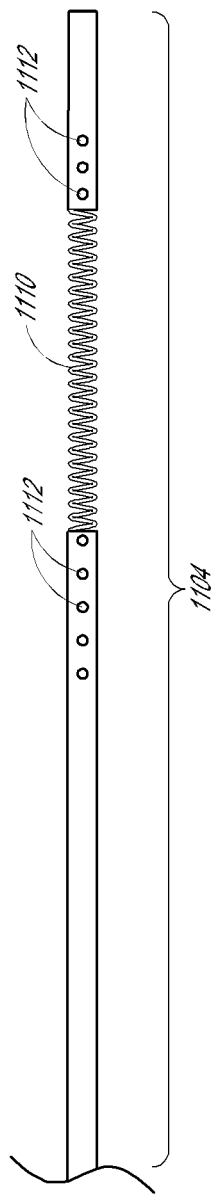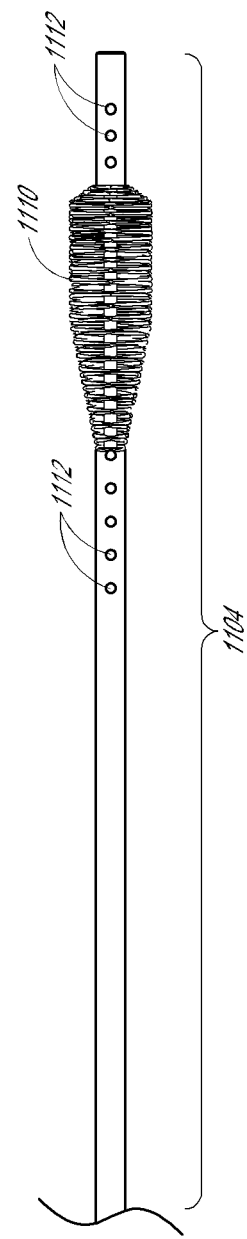

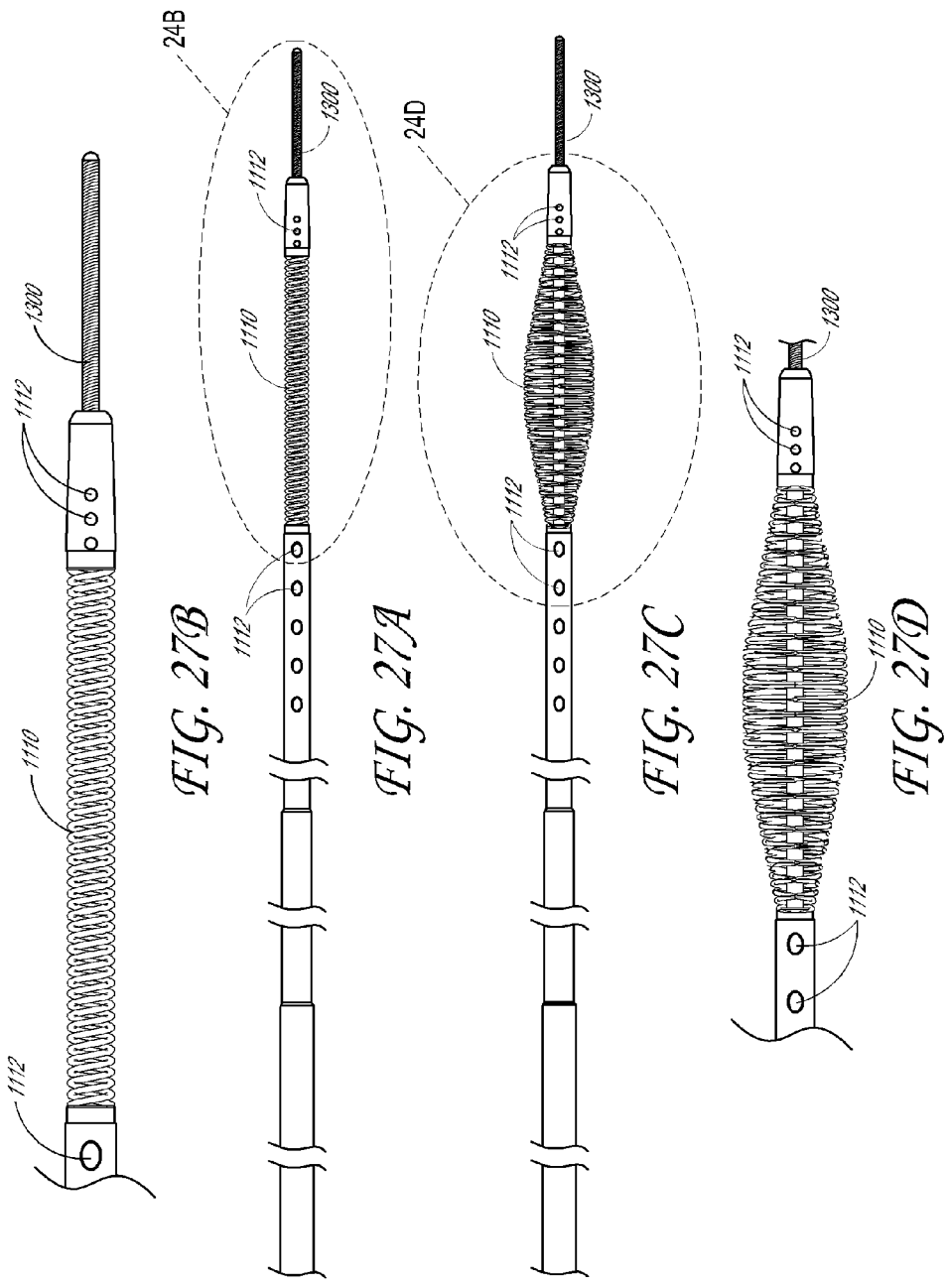

ANEURYSM NECK BRIDGING PROCESSES WITH REVASCULARIZATION SYSTEMS METHODS AND PRODUCTS THEREBY

CROSS-REFERENCE TO RELATED APPLICATIONS

The instant application claims full Paris Convention priority of, and incorporates expressly by reference, U.S. Provisional Application Ser. No. 60/989,422 filed Nov. 20, 2007, and assigned to the instant Assignee, Mindframe, Inc. Likewise, the instant application claims priority to, and incorporates by reference U.S. Provisional Application Ser. No. 61/044,392 filed Apr. 11, 2008; U.S. Provisional Application Ser. No. 61/015,154 filed Dec. 19, 2007; U.S. Provisional Application Ser. No. 60/987,384 filed Nov. 12, 2007; U.S. Provisional Application Ser. No. 61/019,506 filed Jan. 7, 2008; and U.S. Utility application Ser. No. 12/123,390 filed May 19, 2008, each as if fully set forth herein.

BACKGROUND OF THE INVENTION

The present disclosure relates to minimally invasive and catheter delivered intra-cranial aneurysm therapies and revascularization systems for use in the vasculature, especially those suited for usage above the juncture of the Subclavian Artery and Common Carotid Artery. In particular, this disclosure relates to aneurysm neck bridging devices, ostensively emplaced preliminarily, with re-constrainable aspects facilitating their retrieval as needed, which allow for adjunct therapies (such as coils) to be administered. The instant teachings adduce both active and passive revascularization approaches to mitigate deleterious patient imports for those afflicted with acute stroke and/or aneurysmal issues.

SUMMARY OF THE INVENTION

Briefly stated, devices, methods and systems facilitate and enable reconstruction of a vessel wall at the neck of an aneurysm, while revascularization systems promote both active and passive reperfusion/revascularization along with natural and synthetic lysis mechanisms, to mitigate harm to patients with acute and chronic issues, in the neurovasculature.

According to embodiments a cage-like structure is tethered to the end of a trackable distal delivery system. By bridging the neck of an aneurysm while permitting flow, coil embolization, for example, can be performed without risking vessel embolization. The tethered cage-like structure can then be proximally withdrawn, such re-constrainability being optionally waived, as needed for certain therapeutic goals or indications.

According to embodiments, methods and systems function with standard microcatheters to temporarily bridge aneurysmal necks, with the benefits of revascularization being used to mitigate long term harm to patients.

According to embodiments, a novel enhanced system for bridging aneurysms which comprises, in combination at least a microcatheter, a delivery tube, and a tethered cage-like structure which is effective for being emplaced proximate to the neck of an aneurysm, whereby another microcatheter can be threaded there through for coil deployment, delivery of supplemental therapies and related aneurysms addressing approaches.

According to embodiments of the present invention, there are disclosed acute stroke revascularization systems comprising, in combination; catheter systems having guidewires to access and emplace improved neurological medical devices into the cerebral vasculature, the systems including proximal stainless steel pushers with distal nitinol devices.

Along with bridging aneurysms, according to embodiments a novel enhanced tethered revascularization device is deliverable through highly constricted and tortuous vessels, entering a zone associated with subject thrombi/emboli, where deployment impacts the embolus, compacting the same into luminal walls which enables perfusion and lysis of the embolus, while the revascularization device itself remains continuous with the delivery system acting as a filter, basket or stand alone revascularization mechanism, depending on the status of the embolus and other therapeutic aspects of the treatment being offered for consideration.

According to embodiments, there is provided an improved neurological medical device which comprises, in combination, a catheter system effective for delivering an improved aneurysmal neck bridging device detachably tethered to the catheter system which functions in at least three respective modes, including a retracted state and an expanded state; and wherein the device may retract into the retracted state after deployment in an expanded state, in each mode.

According to embodiments, there is disclosed an improved system for bridging aneurysms, comprising; the combination of at least a microcatheter for accessing neurovascular vessels over a guide-wire, a delivery tube, and a tethered cage-like structure which can be delivered to a target site local to an aneurysm and emplaced proximate to the neck of the aneurysm, whereby another microcatheter assembly can be threaded therethrough for delivered supplemental therapy to the aneurysm.

According to the embodiments, a process is disclosed for revascularization while addressing an aneurysm, comprising; providing a catheter-based system with a guide-wire for accessing the cerebral vasculature, housing a tethered cage-like structure within the system, delivering the tethered cage-like structure to a location proximate to an entrance zone of an aneurysm, and expanding the tethered cage-like structure whereby the entrance zone of the aneurysm is bridged.

According to embodiments, there is provided an aneurysm neck bridging products by the processes disclosed, which may be tethered, re-constrained and removed, or emplaced on a longer-term basis.

According to embodiments, there is provided a temporary aneurysm neck bridge device comprising an over-the-wire delivery system further comprised of at least two microcatheters, a tethered cage-like structure expandable from a first to a second position housed within one of the microcatheters, and radiopaque markers.

According to embodiments, there is provided a process comprising in combination providing a revascularization device tethered to a catheter by emplacing the system into a patient for travel to a desired location in a vessel having an obstruction/lesion and deploying the aneurysmal neck bridging and revascularization device by allowing it to move from a first state to a second state along with creating a channel for blood flow as a lytic agent, and removing the system which the obstruction/lesion is addressed.

It is noted that to the extent blood flow does not lyse the blood embolus, lytic agents can be administered via the guidewire lumen, as a feature of the present invention, as would be known to those skilled in the art.

By way of background in the field, the U.S. Food and Drug Administration (FDA) has previously approved a clot retrieval device (The Merci® brand of retriever X4, X5, X6, L4, L5 & L6: Concentric Medical, Mountain View, Calif.). Unfortunately, when used alone, this clot retriever is successful in restoring blood flow in only approximately 50% of the cases, and multiple passes with this device are often required to achieve successful recanalization. IA thrombolytics administered concomitantly enhance the procedural success of this device but may increase the risk of hemorrhagic transformation of the revascularization infarction. There have been several reports of coronary and neuro-stent implantation used for mechanical thrombolysis of recalcitrant occlusions. Taking this approach similarly provides the optimal way to approach and address aneurysms.

In summary, stent placement with balloon-mounted or self-expanding coronary and neuro-types of stents has been shown to be an independent predictor for recanalization of both intracranial and extra cranial cerebro-vasculature occlusions. This provides some insight into approaches needed to overcome these longstanding issues.

By way of example, self-expanding stents designed specifically for the cerebro-vasculature can be delivered to target areas of intracranial stenosis with a success rate of >95% and an increased safety profile of deliverability because these stents are deployed at significantly lower pressures than balloon-mounted coronary stents. However, systems using this data have yet to become commercial, available or accepted by most practitioners.

The use of self-expanding stents is feasible in the setting of symptomatic medium—and large-vessel intracranial occlusions. With stent placement as a first-line mechanical treatment or as a "last-resort" maneuver, TIMI/TICI 2 or 3 revascularization can be successfully obtained, according to clinical data now available.

The literature likewise suggests that focal occlusions limited to a single medium or large vessel, particularly solitary occlusions of the MCA or VBA, may be preferentially amenable to stent placement and thus can help clinicians to achieve improved rates of recanalization. In addition, gender may play a role in the success of self-expanding stent implementation. However, systems need to be designed to execute on this.

Despite increasing utilization of prourokinase rt-PA (recombinant tissue plasminogen activator) or other antithrombotic agents (eg, Alteplase® and Reteplase®), recanalization rates remain approximately 60%. The major concerns with pharmacologic thrombolysis (alone) has been the rate of hemorrhage, inability to effectively dissolve fibrin\platelet-rich clots, lengthy times to recanalization, and inability to prevent abrupt reocclusions at the initial site of obstruction. In PROACTII, ICH with neurologic deterioration within 24 hours occurred in 10.9% of the prourokinase group and 3.1% of the control group (P=0.06), without differences in mortality. Abrupt reocclusions or recanalized arteries has been found to occur relatively frequently, even with the addition of angioplasty or snare manipulation for mechanical disruption of thrombus, and seems to be associated with poor clinical outcomes.

The use of other mechanical means has been reported to be effective in recanalization of acute occlusions. It makes sense that a combination of mechanical and pharmacologic approaches would yield greater benefit.

A known investigation in an animal model has shown, both the Wingspan® brand of self-expanding stent and Liberte® brand of balloon-mounted stent (Boston Scientific, Boston, Mass.) were able to re-establish flow through acutely occluded vessels. The self-expanding stents performed better than the balloon-mounted stents in terms of navigability to the target site. The self-expanding stents incurred lower rates of vasospasm and side-branch occlusions, which suggests superiority of these stents, over balloon-mounted stents, to maintain branch vessel patency during treatment of acute vessel occlusion. In previous animal studies conducted, intimal proliferation and loss of lumen diameter were seen after the implantation of bare-metal, balloon-expandable stents. The literature further supports this set of issues.

These phenomena are believed to be attributable to intimal injury created during the high-pressure balloon angioplasty that is required for stent deployment.

Compared with coronary balloon-mounted stents, self-expanding stents designed for use in the intracranial circulation are superior because they are easier to track to the intracranial circulation and safer to deploy in vessels in which the true diameter and degree of intracranial atherosclerotic disease are unclear.

Moreover, based on previous experience, currently available self-expanding stents provide enough radial outward force at body temperature to revascularize occluded vessels, with low potential for the negative remodeling and in-stent restenosis that are associated with balloon-mounted stents in non intracranial vascular beds.

Because self-expanding stents are not mounted on balloons, they are the most trackable of the stents currently available for the intracranial circulation. Unlike clot retrievers, which lose access to the target (occlusion site) every time they are retrieved (and often to necessitate multiple passes), self-expanding stents allow for wire access to the occlusion at all times, increasing the safety profile of the procedure by not requiring repeat maneuvers to gain access to the target site (as in the case for the Merci® brand of clot retriever).

Self-expanding stent placement of acute intracranial vessel occlusions may provide a novel means of recanalization after failure of clot retrieval, angioplasty, and/or thrombolytic therapy. The patency rates in this series are encouraging, yet issues remain to be addressed.

In the setting of acute stroke, restoring flow is of singular importance. In-stent stenosis or delayed stenosis may be treated in a delayed fashion on an elective basis, should the patient achieve a functional recovery from the stroke.

Recanalization with self-expanding stents may provide flow through the patent artery, and restore flow to the perforators, or, alternatively, they may remain occluded. Restoring flow to the main artery, however, will reduce the stroke burden. What is needed is a solution leveraging positive aspects of stent-based treatment without the negative outcomes which have been associated with traditional stenting.

BRIEF DESCRIPTION OF THE FIGURES

The above-mentioned features and objects of the present invention will become more apparent with reference to the following description taken in conjunction with the accompanying drawings wherein like reference numerals denote like elements and in which:

FIGS. 6A and 6B illustrate an embodiment of a cage-like structure or temporary stent member having a plurality of tether lines;

FIGS. 7A-7D illustrate an embodiment of a cage-like structure or temporary stent member having a plurality of eccentric tether lines;

FIG. 10A-10D illustrate an embodiment of an inner catheter of the acute stroke recanalization system of FIGS. 8 and 9;

FIGS. 12A-12F, 13A-13C, 14A-14D, 15A-15D, 16, 17A-17C, 18, 19, and 20A-20F illustrate various embodiments of revascularization devices;

FIGS. 22A and 22B are perspective views of an embodiment of a method for use of a rapid reperfusion device of the present disclosure;

FIGS. 25A and 25B are perspective views of an embodiment of a rapid perfusion device wherein the active segment comprises a radially expandable wire;

FIGS. 27A-27D are perspective views of an embodiment of a rapid perfusion device wherein the active segment comprises a radially expanding wire mesh.

Figure 1:
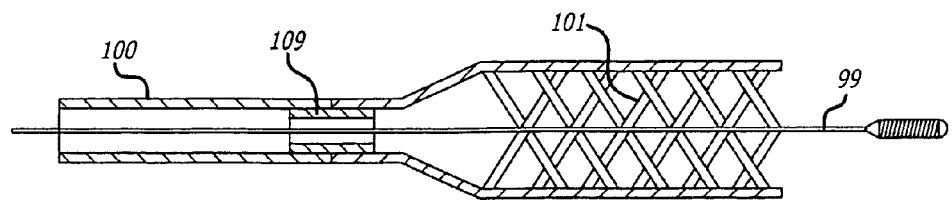
FIG. 1 shows a schematic of a delivery system and exemplary iteration of an embodiment of a temporary aneurysmal treatment device mechanism according to the present invention.

Those skilled in the art readily understand that the merely illustrative figures are not intended to be limiting of the instant teachings, which have been fabricated in various prototype embodiments of defined within the claims appended hereto any further explained in the instant specification.

DETAILED DESCRIPTION OF THE INVENTION

The present inventors have discovered novel ways to treat aneurysms. In short, better treatment options can be offered for consideration than traditionally available, as discussed below. The instant system is optimized in a support role with other therapies. However, use of known and later developed therapies with the instant system differs from prior attempt because revascularization is ongoing while aneurysms are being managed. This applies to vaso-occlusive coil and drug use.

The pathological course of a blood vessel that is blocked is a gradual progression from reversible ischemia to irreversible infarction (cell death). A stroke is often referred to as a "brain attack" and occurs when a blood vessel in the brain becomes blocked or ruptures. An ischemic stroke occurs when a blood vessel in the brain becomes blocked. Ischemic strokes comprise about 78% of all strokes. A hemorrhagic stroke, which account for the remaining 22% of strokes, occurs when a blood vessel in the brain ruptures. Stroke is the third leading cause of death in the United States, behind heart disease and cancer and is the leading cause of severe, long-term disability. Each year roughly 700,000 Americans experience a new or recurrent stroke. Stroke is the number one cause of inpatient Medicare reimbursement for long-term adult care. Total stroke costs now exceed $45 billion per year in US healthcare dollars.

Furthermore, one type of aneurysm, commonly known as a "wide-neck aneurysm" is known to present particular difficulty in the placement and retention of vaso-occlusive coils. Wide-neck aneurysms are herein referred to as aneurysms of vessel walls having a neck or an "entrance zone" from the adjacent vessel, which entrance zone has a diameter of either (1) at least 80% of the largest diameter of the aneurysm; or (2) is clinically observed to be too wide effectively to retain vaso-occlusive coils that are deployed using the techniques discussed herein. The instant system addresses and understands this issue and provides an approach which has clinical improvements over known systems.

Vaso-occlusive coils lacking substantial secondary shape strength may also be difficult to maintain in position within an aneurysm no matter how skillfully they are placed. This may also be true of coils that have a secondary shape. For example, a 3D coil that takes a spherical shape may be herniated out of the aneurysm into the parent vessel if the neck is too wide. Using the device of the present invention permits the coils to be held in the aneurysm until a critical mass of coils is achieved within the aneurysm so that the coil mass will not move when the device is withdrawn.

A few devices have been disclosed for maintaining the presence of vaso-occlusive coils within an aneurysm. One such device is a retainer for retaining coils within the aneurysm cavity. The retainer device is released into the vessel exterior to the aneurysm. The device is held in place via the presence of radial pressure on the vessel wall. After the device is released and set in an appropriate place. A microcatheter is inserted into the lumen so that the distal end of the catheter is inserted into the aneurysm cavity. One or more vaso-occlusive devices is then introduced into the aneurysm cavity. The retainer device maintains the presence of the vaso-occlusive devices within the aneurysm whether it is a large-mouth aneurysm or not.

Another approach to filling intracranial aneurysms includes the use of injectable fluids or suspensions, such as microfibrillar collagen, various polymeric beads, and polyvinyl alcohol foam. These polymeric agents may additionally be crosslinked, sometimes in vivo to extend the persistence of the agent at the vascular site. These agents may be introduced into the vasculature through any of a variety of known catheters. After introduction, the deployed materials form a solid space-filling mass. Other materials, including polymeric resins, typically cyanoacrylates, hydrogels and other gels, fibrin glues, and calcium binding seaweed extracts are also employed as injectable vaso-occlusive materials. These materials may be mixed with a radio-opaque contrast material or made radio-opaque by the addition of a tantalum powder.

The delivery of liquid embolic agents into aneurysms in general has numerous obstacles. The viscosity of the material makes delivery difficult, and leads to run on even after the pressure head has been removed from the delivery catheter. Inadequate opacification of the material makes it difficult to see. As a result it can leak into the parent vessel. This can result in vessel occlusion and distal embolization into the organs vascular bed. To date, these materials have been delivered using an inflated balloon adjacent to the abnormality to be treated. Inflation of the balloon during delivery leads to temporary vessel occlusion and can result in downstream organ ischemia and even infarction.

A further microcatheter may be introduced either or both alongside or through an internal lumen of the delivery wire/pushwire delivering the neck-bridge so as to also permit the introduction of an embolitic agent into the aneurysm through, around or adjacent the mesh of the scaffold which has opened spaces or cells which permit that microcatheter and delivery wire to introduce that embolitic agent into the aneurysm. Such an agent may be comprised of metallic or plastic coils, or alternatively a combination of plastic and metal braid or composite plastic and metal braid and/or liquid or polymerized polymeric agents, or biologic components of blood and plasma like thrombin, fibrin or any biologic materials like DNA, RNA plasmids or the like, to embolize within that aneurysm.

However, after, or perhaps during, delivery of such a coil into the aneurysm, there is a risk that a portion of the coil might migrate out of the aneurysm entrance zone and into the feeding vessel. This is especially true in aneurysms where the diameter of the aneurysm neck approaches the diameter of the aneurysm body in a 1:1 ratio. The presence of such a coil in that feeding vessel may cause the undesirable response of causing an occlusion there. Also, there is a quantifiable risk that the blood flow in the vessel and the aneurysm may induce movement of the coil farther out of the aneurysm, resulting in a more thoroughly developed embolus in the patent vessel. Being that coils are constructed from very low gauge wire, the coil mass can compact resulting in aneurysm recanalization. Thus, it is important to consider needs that can be addressed for aneurysms, given the need for ongoing perfusion.

By way of reminder, there are only two FDA-approved mechanical treatment options for an acute ischemic stroke. One option is a thrombo-embolectomy device. In August of 2004, Concentric Medical received FDA approval for its MERCI™ brand of clot removal device. The Merci device is designed to capture an embolus or clot and remove it from the blocked vessel thereby restoring blood flow.

The device is designed to be used in conjunction with a microcatheter. The microcatheter must cross the embolus before the Merci device can be deployed. The Merci device design is a cork-screwed guidewire. This device is only able to capture and remove matter that is firm or held together by itself. In most cases Merci breaks up the embolus rather than removes it and is used in combination with drug therapy to restore blood flow. A typical procedure using Merci will take 2-3 hours to restore blood flow if at all and may take multiple passes through the vessel to either capture, macerate or open the vessel. In some cases, the Merci device may capture an embolus but then lose grasp of it and deposit it incidentally in another area of the neuro vasculature creating a new stroke in a new territory. In some cases complications such as vessel dissection, perforation and hemorrhage arise as a result of manipulation in the vessel. Some issues in using Merci are that the Merci device itself is a guidewire. Therefore, once it is removed, access is lost. Also, as the device is engaging an embolus and being withdrawn proximally, the vessels tend he pulled with the device and buckle. This actions appears to be a great source for the embolus fragmenting and vessel damage. A second option is an aspiration device manufactured by Penumbra, Inc. The embolus is removed by aspirating or sucking from the proximal side. A microwire is passed through the catheter and into the embolus to aide is aspirating.

Provide a device or therapy where blood can be reperfuse or an embolus or blood clot can he removed from the neurovasculature consistently and safely with arterial support and maintain access throughout the procedure.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the micro catheter is placed within the sac of the aneurysm, and the microcatheter is used to place embolic material into the sac of the aneurysm. The embolic material includes, for example, detachable coils or an embolic agent, such as a liquid polymer. The placement of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being placed. Therefore, there is a risk of overfilling the aneurysm in which case the detachable coils also herniate or prolapse into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus the aneurysm can recanalize.

Embolic agent migration is also a problem. For instance, where a liquid polymer is placed into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

Using endovascular techniques self-expandable tethered or reconstrainable self-expanding neurological medical devices offer instant revascularization/recanalization of MCA's and related vessels, without any of the traditional concerns associated with stenting, according to embodiments of the present invention.

Expressly incorporated herein by reference are the following U.S. Letters patents and publications, each which has been examined and is distinguished from the instant filing as if fully set forth herein: 2005/0119684; 2007/0198028; 2007/0208367; U.S. Pat. Nos. 5,972,019; 5,928,260; 6,066,158; 6,190,358; 6,210,364; 6,605,057; 6,685,722; 7,147,655; 7,160,317; 7,172,575; 7,175,607; and 7,201,770.

The instant system allows for covering an aneurysm opening in an intracranial aneurysm, for temporary or longer term placement in addition to allowing for natural lysis, including revascularization of the challenged vessels, and importantly radially filters any particulates generated, to obviate the need to be concerned with distal migration of the same, unlike prior systems or applications which include largely "off-label" usages of devices approved only for aneurysms in the brain.

The present disclosure relates to improved aneurysmal neck bridging device and revascularization devices used to treat, among other things, ischemic stroke. Naturally, therefore, the revascularization devices of the present disclosure are designed to be used in neuro-type applications, wherein the specifications of the present catheters and revascularization devices may be deployed in the blood vessels of the cerebral vascular system. Similarly contemplated for the revascularization systems and catheters of the present disclosure is deployment in other parts of the body wherein the specifications of the present disclosure may be used in other vessels of the body in a non-invasive manner.

According to embodiments, disclosed herein is a catheter-based revascularization system. The revascularization devices of the present disclosure are for revascularization of blood vessels. When the catheter-based revascularization system of the present disclosure is deployed into a blood vessel having an embolus, the revascularization device is expanded thereby opening the vessel so that the vessel can resume proper blood flow.

According to the instant teachings, deployment of the system of the present disclosure establishes immediate 50% of the diameter of the lumen patency of the vessel being addressed. Among the prior art, no system having adequately small profile with flexibility to promote improved access for in-site treatment is known which may be used as a temporary (not implanted) solution. Those skilled in the art readily understand that detachment methods comprising mechanical, electrical, hydraulic, chemical, or thermal, and others are within the scope of the instant teachings.

Moreover, as the embolus dissolves, either via blood flow or by infusing lytic agents than the guidewire lumen, the deployed revascularization device radially filters larger embolus particles from traveling downstream, thereby reducing the chances of further complications. Once the blood vessel is revascularized, the revascularization device is modified to be in a removable state together with filtered detritus, and the catheter-revascularization system is removed from the blood vessels of the patient.

Likewise, in the event that no resolution of the embolus is noted in the instant revascularization system the inventors contemplate detachment and employment as a stent of the cage-like membrane. Angiographic recanalization has been associated with improvement in clinical outcome in the setting of acute stroke resulting from acute intracranial thrombotic occlusion. Anatomic limitations (tortuous anatomy, length of the occlusion, or location of occlusion) or supply limitations are among the reasons precluding use of prior art systems until the adverse of the instant teachings.

Stenting has been used successfully to restore flow after abrupt reocclusion occurring after recanalization with other modalities in previous cases. Stenting has also been reported in cases in which other modalities have failed to recanalize vessels. Even if an underlying stenosis is rarely the cause of stroke, stenting may play a role by morselizing the embolic clot or trapping it against the arterial wall.

The use of intracranial stents as a method for arterial recanalization during cerebral ischemia caused by focal occlusion of an intracranial vessel has been demonstrated to have benefits in some cases. Despite the use of available pharmacological and mechanical therapies, angiographic recanalization of occluded vessels has not been adequately achieved before stent placement, in most cases.

When SAH and intracranial hematoma occurred in patients in whom balloon-mounted stents were used, they most likely resulted from distal wire perforation. The distal wire purchase needed to navigate a coronary stent into the intracranial circulation may explain the occurrence of these adverse events. Alternatively, multiple manipulations of the Merci® brand of retriever device or expansion of balloon-mounted stents may have induced microdissections in the vessel. Stents designed for intracranial navigation have better navigability and pliability. The Wingspan® brand of stent (Boston Scientific) was designed to have more radial force than the Neuroform® brand of stent and may further improve this technique. However, the act clearly needs to advance further in this area.

IA therapy for stroke has evolved during the past decade. Approval of the Merci® brand of retriever device represents a significant step toward achieving better outcomes in acute stroke for patients not suitable for IV tPA. However, recanalization is not always achieved using this device. Therefore, additional treatment options are required, as offered for consideration herein.

Spontaneous dissection of the internal carotid artery (ICA) is one of the main causes of ischemic stroke in young and middle-aged patients, representing 10% to 25% of such cases. Because infarct due to dissection is mainly thromboembolic, anticoagulation has been recommended to prevent new stroke in patients with acute dissection, provided they have no contraindications. In the acute phase, intravenous recombinant tissue-type plasminogen activator (IV rtPA) given within 3 hours after onset of stroke due to dissection is reportedly safe and effective. However, this often needs supplemental therapy to be effective.

Endovascular treatment with stent deployment for ICA dissection with high-grade stenosis or occlusion may be most appropriate when anticoagulation fails to prevent a new ischemic event. In such cases, the MCA may be patent. However, to compare outcomes of patients with acute stroke consecutive to MVA occlusion due to ICA dissection treated either by stent-assisted endovascular thrombolysis/thrombectomy or by IV rtPA thrombolysis. Stent assisted endovascular thrombolysis/thrombectomy compared favorably with IV rtPA thrombolysis, underscoring the need for the instant device.

The main limitation of this procedure is the immediate need for an experienced endovascular therapist. The number of cases of MCA occlusion due to carotid artery dissection was quite small and represented <10% of patients admitted for carotid dissection. However, despite these promising preliminary results, potential drawbacks related to the procedure must be considered. Acute complications such as transient ischemic attack, ischemic stroke, femoral or carotid dissection, and death have been reported. Other potential hazards of endovascular treatment of carotid dissection could have been observed. On balance, the risk-benefit favors solutions like the present invention.

Most patients with acute cerebrovascular syndrome with MCA occlusion consecutive to ICA dissection have poor outcomes when treated with conventional IV rtPA thrombolysis, whereas most patients treated with stent-assisted endovascular thrombolysis/thrombectomy show dramatic improvements. Further large randomized studies are required to confirm these data, which trends likewise are technical bases for the instant systems.

Cerebral aneurysms occur in approximately 2% of the population. Approximately 30,000 aneurysms are treated annually in the USA. Aneurysms grow from a weakness in a blood vessel. Origins of aneurysms are presently unknown but linked to hypertension and injury.

About 80% of aneurysms are less than 10 mm with the remainder growing to as large as 40 mm. Most large aneurysms have wide necks characterized with a neck greater than 4 mm or a dome to neck ratio less than 2:1.

In cases when aneurysms have a wide neck, either stent-assisted coiling in practice or balloon remodeling is performed to embolize the aneurysm. During stent-assisted coiling, a stent (for example, the Boston Scientific® brand of Neuroform™ system or the Johnson & Johnson Cordis Enterprise™ brand of) structure is placed within the artery of the vessel with the aneurysm in an attempt to reconstruct the vessel wall at the neck of the aneurysm.

Patients are typically anti-coagulated and anti-aggregated with a combination of aspirin and Plavix to mitigate the thrombo-embolic effects of a foreign body response. The patients will maintain the drug regimen long after the embolization procedure.

However, patients with sub-arachnoid hemorrhage (SAH) are not candidates for stents due the prophylactic drug regimen to mitigate the thrombo-embolic complications. A second approach is to perform balloon-remodeling. In this technique, a very soft, conformable balloon (the eV3 brand of Hyperform device™) typically used for balloon-test-occlusion is placed in the artery at the neck to reconstruct the neck at the aneurysm origin. However, during this technique, flow arrest is performed while the balloon is inflated.

There is a risk of initiating an ischemic event during balloon remodeling and/or a thrombo-embolic event during flow arrest. This technique can be used during SAH because no additional prophylactic drug regimen is required. Once both these techniques are performed, coil embolization of the aneurysm can be performed. During the stenting procedure, the stent is permanently implanted. During balloon remodeling, the balloon is removed once embolization is completed.

A device that can reconstruct the vessel wall at the aneurysm neck origin has been created by tethering a cage-like structure to the distal end of a trackable delivery system. For example, the MindFrame® brand of cage-like structure tethered stent (Lake Forest, Calif.) can be placed across the neck of aneurysm without prophylactically administered aspirin and Plavix as well as not obstructing flow. The tethered stent allows perfusion through the body of the structure and provides support to the neck of the aneurysm allowing coil embolization procedure the tethered stent can then be withdrawn proximally into the standard delivery microcatheter. In one embodiment, the cage-like structure comprises radiopaque markers. The radiopaque markers can be comprised of at least one of platinum and gold pegs pressed into pre-laser cut holes. In one embodiment, the cage-like structure is comprised of variable cell sizes.

The device is delivered through standard microcatheters currently available to the interventionalist. An embolization microcatheter can either be placed into the "aneurysm prior to placement of the tethered stent or after placement of the tethered stent. If the latter is preferred then the coil embolization microcatheter must be placed through the struts of the tethered stents to access the body of the aneurysm to commence coiling. Both techniques are performed during standard stenting procedures.

Referring now to FIG. 1, delivery tube 100 deploys tethered cage-like device 101 prior to embolization, using a standard over-the-wire (OTW) system including guide-wire 99. The instant system is able to be deployed prior to embolization, used to reconstruct the arterial wall at the aneurysm neck, hold in place emboli material and then be able to be removed after embolization of the aneurysm sac is complete. Those skilled in the art understand how the present invention functions with revascularization efforts need to address for example, stroke.

The system provides a method to assist in aneurysm embolization that does not restrict blood flow and can be used without placing patients on ASA/Plavix during Embolization. During balloon remodeling, flow arrest is performed. During stenting, patients need ASA/Plavix.

According to the invention, the present system uses both passive and active reperfusion to address aneurysms without the detriments of balloon re-modeling. A temporary tethered cage-like structure 101 is non-detachable in some embodiments but attached either to a hypotube or guide-wire 99 allowing it to be navigated into tortuous vasculature in the brain. The device and system are deployed prior to embolization, as discussed above and claimed below. Device 101 may be attached to guide-wire 99 or tube 100, as discussed.

Figure 2:
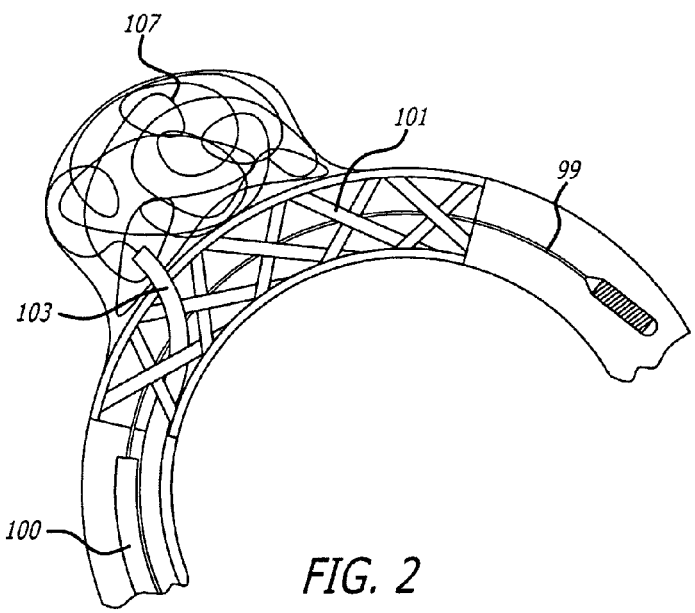
FIG. 2 shows an emplaced temporary aneurysmal treatment device and mechanism bridging the neck of an aneurysm, according to the present invention.
Figure 3:
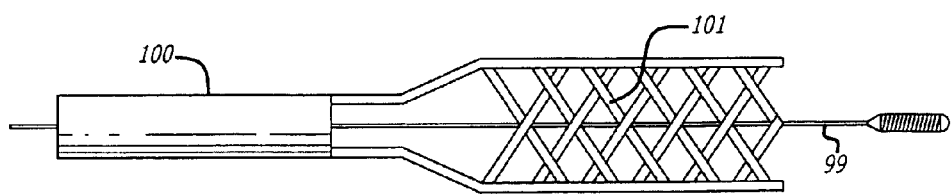
FIG. 3 likewise schematically depicts a delivery system with embodiments of a device according to the instant teachings.
Figure 4:
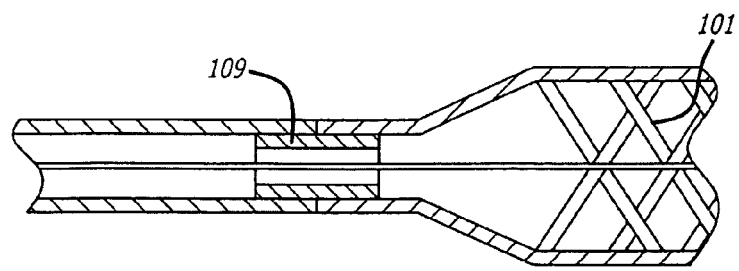
FIG. 4 further illustrates systems according to the instant teachings.

Referring also to FIG. 2 through FIG. 4, microcatheter/delivery tube 100 emplaces cage-like structure 101 at aneurysm neck, while a coiling microcatheter 103 accesses the aneurysm, and allows coil 107 to be placed therein. Delivery tube 100 and cage-like structure 101 are known in the art and may include Nitinol® or the like "super-elastic" materials, as detailed below.

FIG. 3 likewise provides further details of the instant system, with tethered cage-like structure 101 being released from delivery tube 100 using known OTW techniques.

Figure 5:
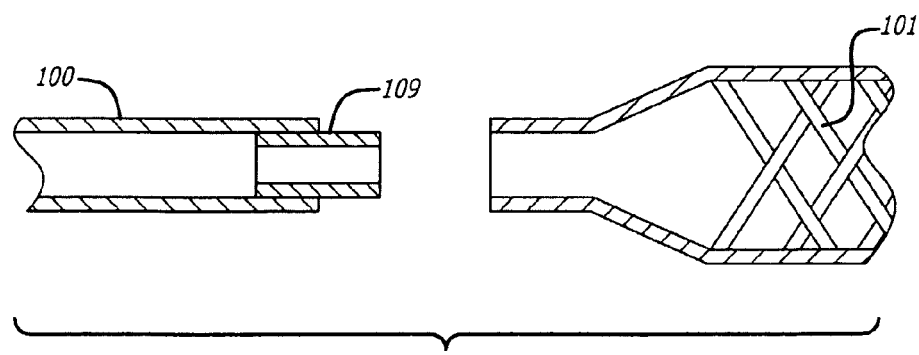
FIG. 5 schematically illustrates additional features according to embodiments of the instant system.

FIG. 4 and FIG. 5 likewise show intermediate steps, whereby placement of the system allows an aneurysm to be isolated, at the neck, whereby coils 107 may be used. According to embodiments illustrated by FIG. 5, if coil 107 somehow gets caught in cage-like structure 101, it may be impossible to remove the device without causing damage to or rupturing the vessels. Therefore, according to embodiments, cage-like structure 101 may be detachable (e.g., via attachment mechanism 109), enabling it to be left in the vessel in the event of a complication where it cannot be safely removed, or as needed otherwise.

The delivery tube 100 is a variable stiffness tube that is able to track to and through the tortuous anatomy of the cerebral vasculature (i.e., internal carotid artery, MCA, ACA, vertebral and basilar).

The delivery tube 100 can be one or two pieces but must have greater proximal pushability (stiffness) and greater distal flexibility (softness) to allow tracking to distal cerebral arteries.

The delivery tube 100 should also have a lumen that enables tracking over a guide-wire. This feature provides a few benefits; ability to track and be delivered; ability to maintain access in the event different size devices need to be exchanged; provide support to arterial tree during device deployment and recovery. A flexible device may tend to herniate or prolapse into openings. The guide-wire provides a pathway (concentric) to the artery and supports the device preventing such technical complications.

The delivery tube 100 can be mechanically attached to the cage-like structure by soldering, welding or press fitting. Likewise, those skilled in the art readily understand their attachment mechanisms 109.

The cage-like structure is made of Nitinol to allow it to be compressed and loaded into an introducer for packaging. Similarly memory-based materials likewise function, in accordance with the instant systems.

The introducer enables the device to be transferred into a microcatheter and deploy to a trusted location such as a aneurysm neck.

The tethered cage-like structure is attached to the delivery wire described previously.

By attaching it to a delivery wire, the cage-like structure can be placed, retracted, repositioned and recaptured into a microcatheter.

This is an important feature. The device, being temporary, allows for the following: 1) perfusion of blood through artery during coiling; 2) perfusion from coiling herniation or prolapse; and 3) removal of the device, mitigating the use of Aspirin and Plavix. The Jervis patents are well know and likewise expressly incorporated herein by reference, including U.S. Pat. No. 6,306,141.

A technical basis for the term "super-elastic" is found in the class of nickel-titanium alloys known as "nitinol" alloys discovered by the United States Navy Ordinance Laboratory. These materials are discussed in length in U.S. Pat. No. 3,174, 851 to Beuhler, et al; U.S. Pat. No. 3,351,463 to Rozner, et al; and U.S. Pat. No. 3,753,700 to Harrison, et al. Alloys known to be suitable for this invention are those containing at least 1.5% (wt) and up to about 85% (wt) or more, of one or more alloying members selected from the group consisting of vanadium, chromium, manganese, iron, and cobalt. By the term "stent" or "ribbon", we intent do include elongated shapes, the cross section of which are not square or round and may typically be rectangular, oval, or semi-oval. They should have an aspect ratio of 0.05 (thickness/width) or less, depending on application at issue.

FIGS. 6A and 6B illustrate a side view and a perspective view of an embodiment of a cage-like structure or temporary stent member 601 having a plurality of tether lines 602. The cage-like structure 601 includes apertures 603 configured to receive radiopaque markers FIGS. 7A-7D illustrate side, front, back and section views of an embodiment of a cage-like structure or temporary stent member 701 having a plurality of eccentric (e.g., off-center tether lines 702.

Figure 8:
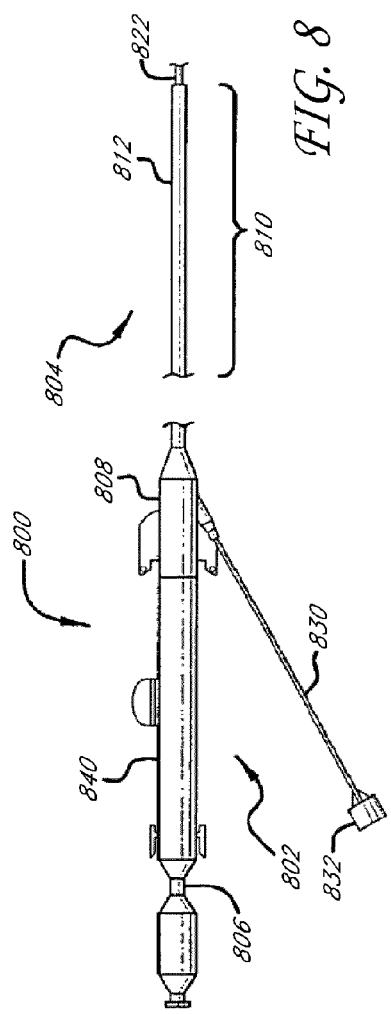
FIG. 8 is a perspective view of an embodiment of an acute stroke recanalization system according to embodiments of the present disclosure in a first configuration.

As excerpted from U.S. application Ser. No. 12/123,390 filed May 19, 2008 and from U.S. Provisional Nos. 60/989, 422 filed Nov. 20, 2007 and 61/044,392 filed Apr. 11, 2008, each of which are incorporated herein by reference, FIGS. 8, 9, 9A, 10A-10D and 11 illustrate various embodiments of revascularization devices. According to embodiments and as illustrated in FIG. 8, catheter-based revascularization system 800 provides a platform for lysing emboli in occluded blood vessels. Accordingly, catheter-based revascularization system 800 generally comprises control end 802 and deployment end 804. According to embodiments, control end 802 is a portion of the device that allows a user, such as a surgeon, to control deployment of the device through the blood vessels of a patient. Included as part of control end 802 is delivery handle 806 and winged apparatus 808, in some embodiments. Those skilled in the art readily understand module 813 (see FIG. 9) is detachable.

According to some examples of the instant system during shipping of catheter-revascularization system 800, shipping lock (not shown) is installed between delivery handle 806 and winged apparatus 808 to prevent deployment and premature extension of revascularization device 824 (see FIG. 9) while not in use. Furthermore, by preventing delivery handle 806 from being advanced towards winged apparatus 808, coatings applied to revascularization device 824 are stored in a configuration whereby they will not rub off or be otherwise damaged while catheter-based revascularization system 800 is not in use.

According to embodiments, agent delivery device 830 provides a conduit in fluid communication with the lumen of the catheter-based revascularization system 800 enabling users of the system to deliver agents through catheter-revascularization system 800 directly to the location of the embolus. The instant revascularization system delivery device may be made from materials known to artisans, including stainless steel hypotube, stainless steel coil, polymer jackets, and/or radiopaque jackets. In one embodiment, the revascularization systems comprise a plurality of apertures 818 allowing infusable lytic agents to exit radially and distally into at least a subject embolus when transmitted through agent delivery device which is in fluid communication therewith. The revascularization systems according to several embodiments herein can comprise radiopacity for imaging purposes.

Accordingly, luer connector 832 or a functional equivalent provides sterile access to the lumen of catheter-based revascularization system 800 to effect delivery of a chosen agent. Artisans will understand that revascularization devices of the present invention include embodiments made essentially of nitinol or spring tempered stainless steel. Revascularization devices likewise may be coated or covered with therapeutic substances in pharmacologically effective amounts or lubricious materials. According to embodiments, coatings include nimodipine, vasodialators, sirolamus, and paclitaxel. Additionally, at least heparin and other coating materials of pharmaceutical nature may be used.

Deployment end 804 of catheter-based revascularization system 800 comprises proximal segment 810 and distal segment 820. Proximal segment 810, according to embodiments, houses distal segment 820 and comprises outer catheter 812 that is of a suitable length and diameter for deployment into the blood vessel of the neck, head, and cerebral vasculature. For example in some embodiments, proximal segment 810 is from at least about 100 cm to approximately 115 cm long with an outer diameter of at least about 2.5 French to about 4 French.

Figure 9:
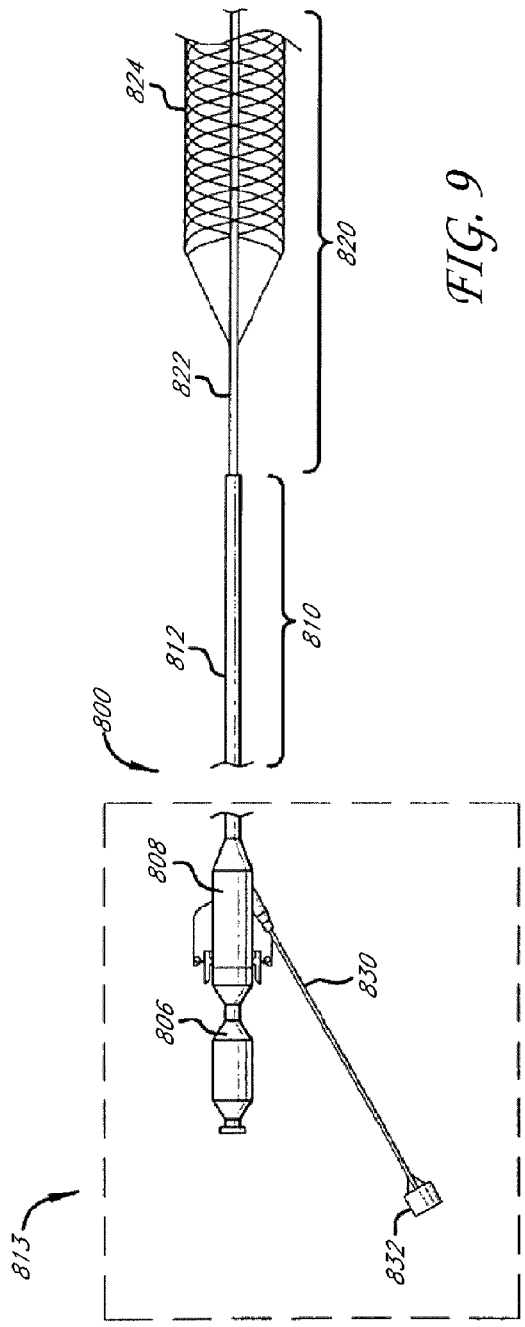
FIG. 9 is a perspective view of an embodiment of an acute stroke recanalization system according to embodiments of the present disclosure tailored for use with the neurovasculature in a second configuration, further illustrating modular aspects of the system as used with tethered or reconstrainable self-expanding neurological medical devices.
Figure 9A:
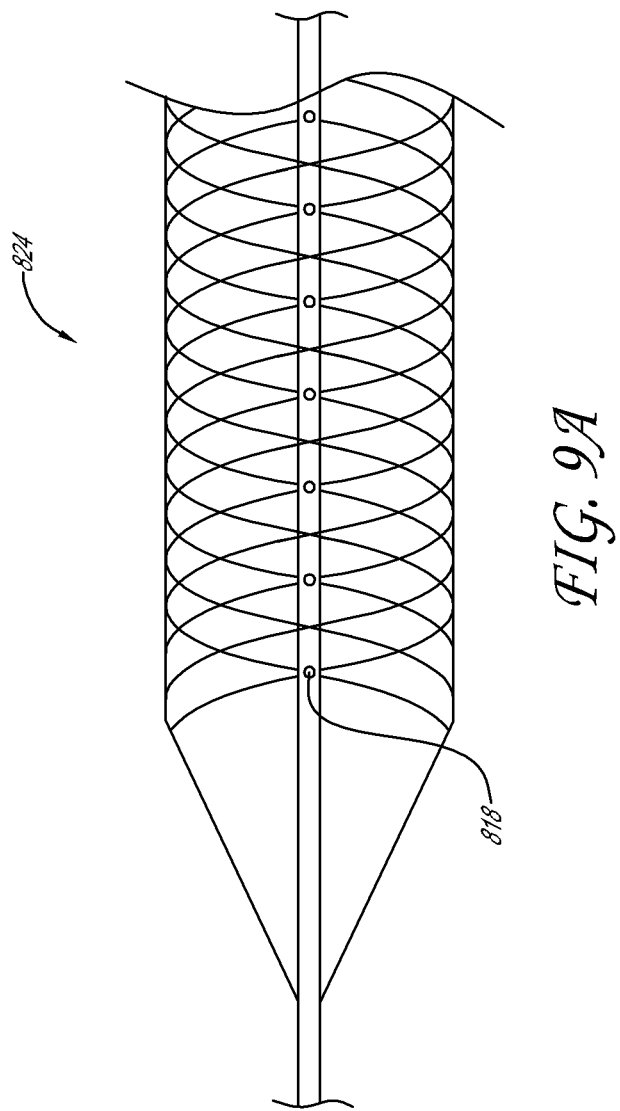
FIG. 9A illustrates a detailed view of the inner catheter of FIG. 9.

Referring also to FIG. 9, distal segment 820 comprises inner catheter 822 and revascularization device 824 (as shown here in one embodiment having uniform cells, variable cells likewise being within other embodiments of the present invention), which is connected to inner catheter 822. Inner catheter 822, according to embodiments, is made from stainless steel coil, stainless steel wire, or ribbon or laser cut hypotube and is of a suitable length and diameter to move through outer catheter 812 during deployment. For example, inner catheter 822 extends from outer catheter 812 38 cm, thereby giving it a total length of between at least about 143 and 175 cm (or between about 143 and 150 cm). The diameter of inner catheter 822 according to the exemplary embodiment is 2.7 French, with an inner diameter of at least about 0.012 to 0.029 inches (or at least about 0.012 to 0.021 inches). The inner diameter of inner catheter 822 may be any suitable diameter provided inner catheter 822 maintains the strength and flexibility to both deploy and retract revascularization device 824. In one embodiment, an inner catheter 822' comprises a variable-pitch hypotube, as shown in FIGS. 10A-D. In some embodiments, the hypotube has an outer diameter of 0.025", 0.022", or 0.016" and an inner diameter of 0.017" or 0.008". In some embodiments, the hypotube comprises a 25TW hypotube or a 31TW hypotube. In one embodiment, the inner catheter 822' comprises a laser-cut, variable-pitch hypotube. Region L comprises a laser cut transition region of the variable-pitch hypotube. Regions P1, P2 and P3 comprise three regions of the variable-pitch hypotube having variable pitch. In one embodiment, the pitch decreases from region P1 to region P2 and from region P2 to region P3.

Referring to FIGS. 8 and 9, revascularization device 824 is a self-expanding, reconstrictable retractable device tethered to inner catheter 822. Revascularization device 824 may be made from nitinol, spring tempered stainless steel, or equivalents as known and understood by artisans, according to embodiments. Revascularization device 824, according to embodiments and depending on the particular problem being addressed, may be from at least about 3.5 mm to about 50 mm in its expanded state. In an expanded state, revascularization device 824 is designed to expand in diameter to the luminal wall of blood vessel where it is deployed.

As known to artisans, revascularization device 824 may be coated or covered with substances imparting lubricous characteristics or therapeutic substances, as desired. Naturally, the expandable mesh design of revascularization device 824 must be a pattern whereby when revascularization device 824 is retracted, it is able to fully retract into inner catheter 822. The nature of the cell type likewise changes with respect to the embodiment used, and is often determined based upon nature of the clot.

Figure 11:
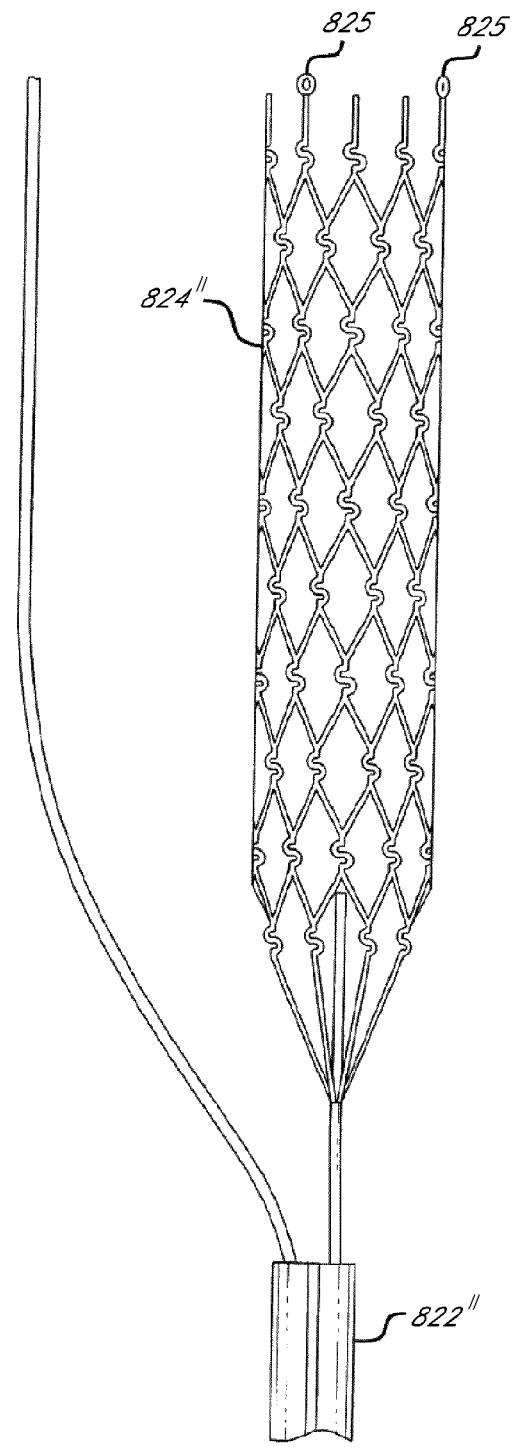
FIG. 11 illustrates an embodiment of a stroke device.
Figure 12A:
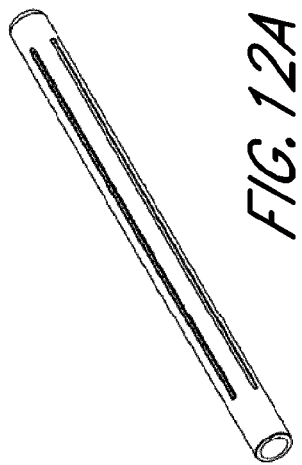
Figure 12B:
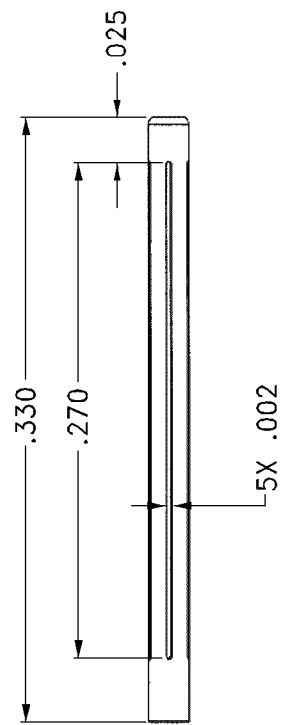
Figure 12C:
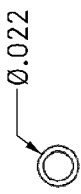
Figure 13A:
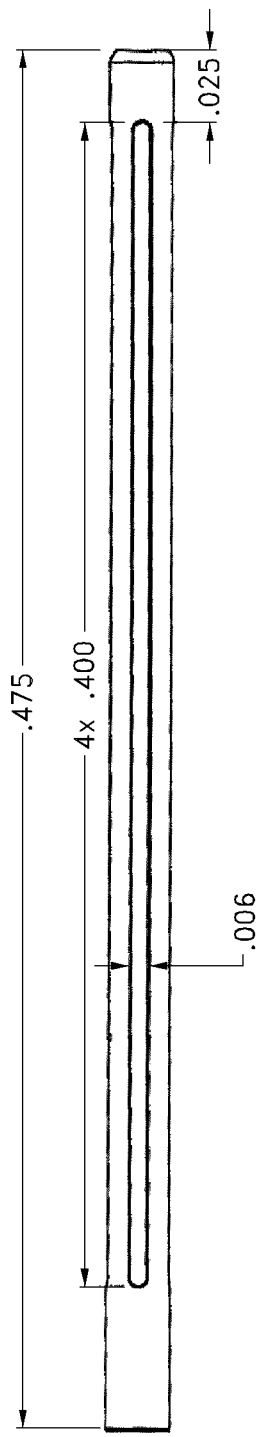
Figure 13B:
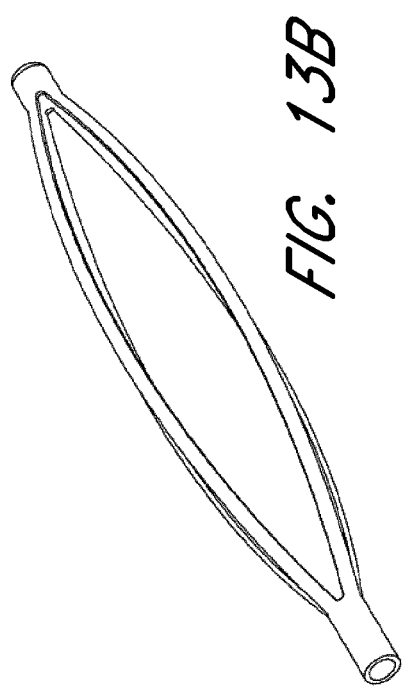
Figure 13C:
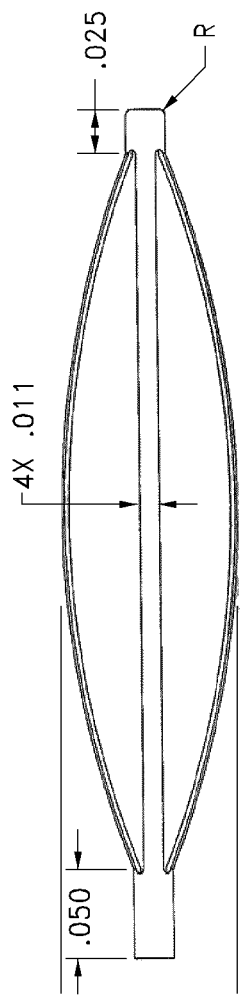
Figure 14A:
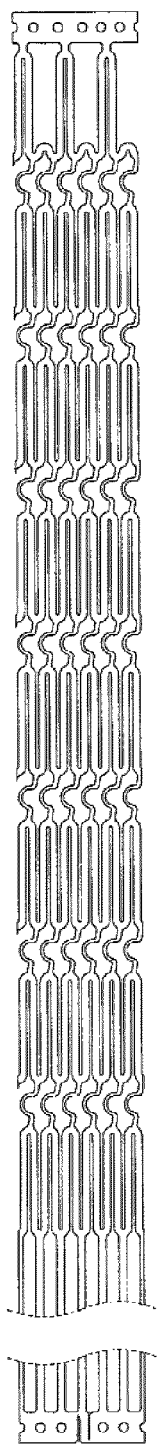
Figure 14B:
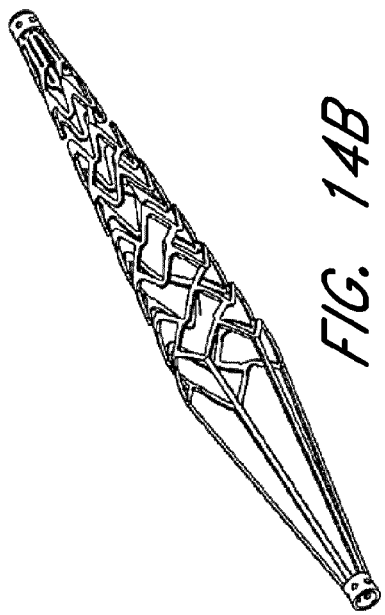
Figure 14C:
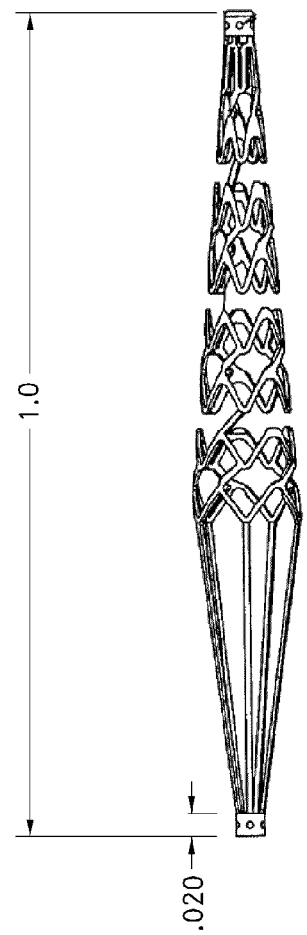
Figure 14D:
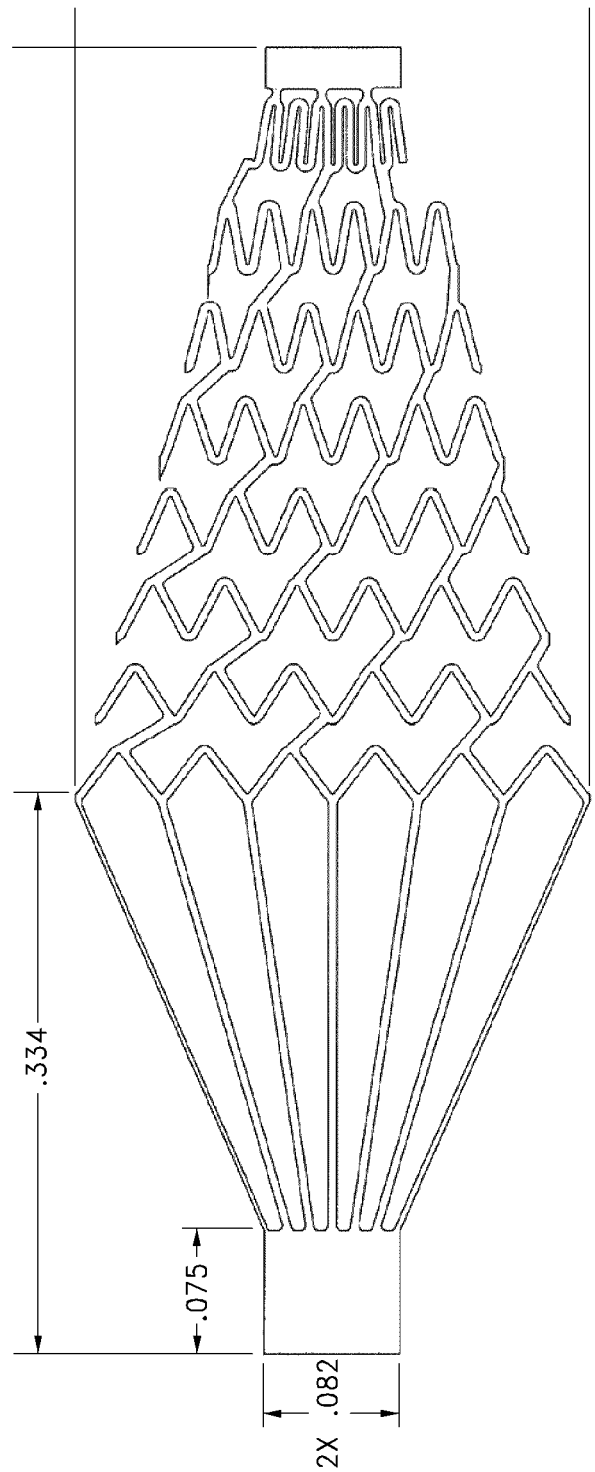
Figure 15A:
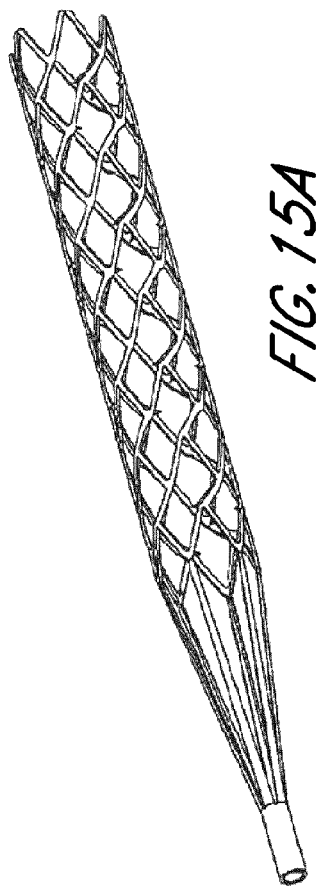
Figure 15B:
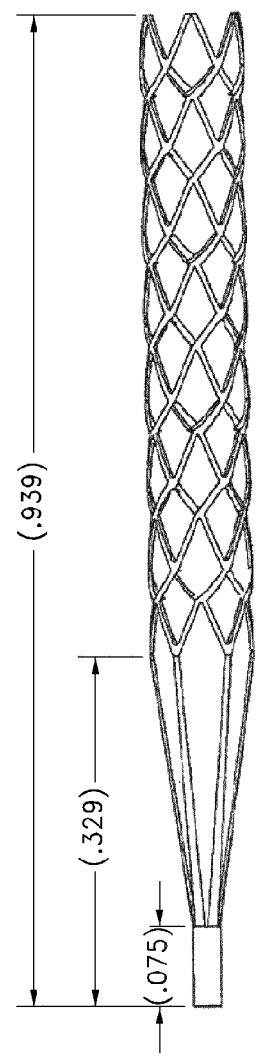
Figure 15C:
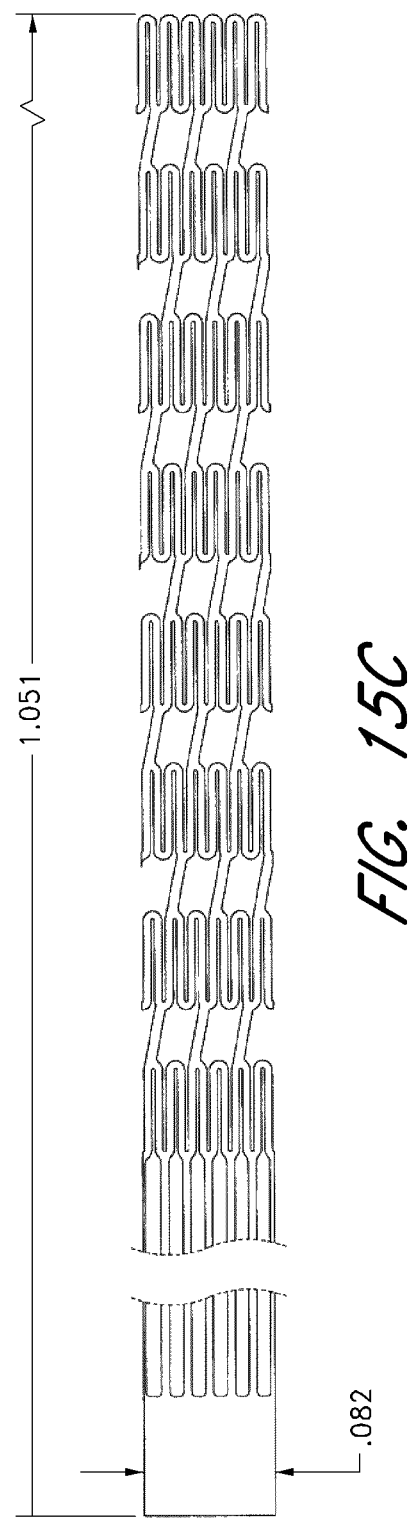
Figure 16:
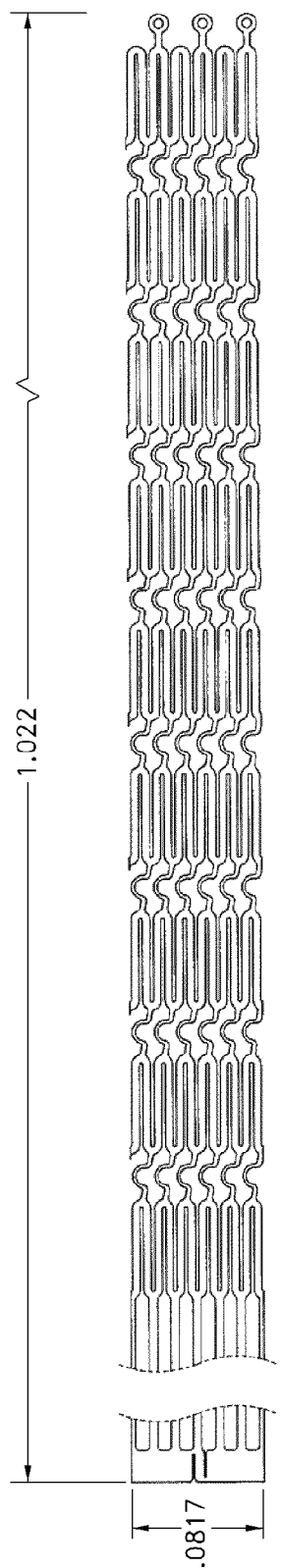
Figure 17A:
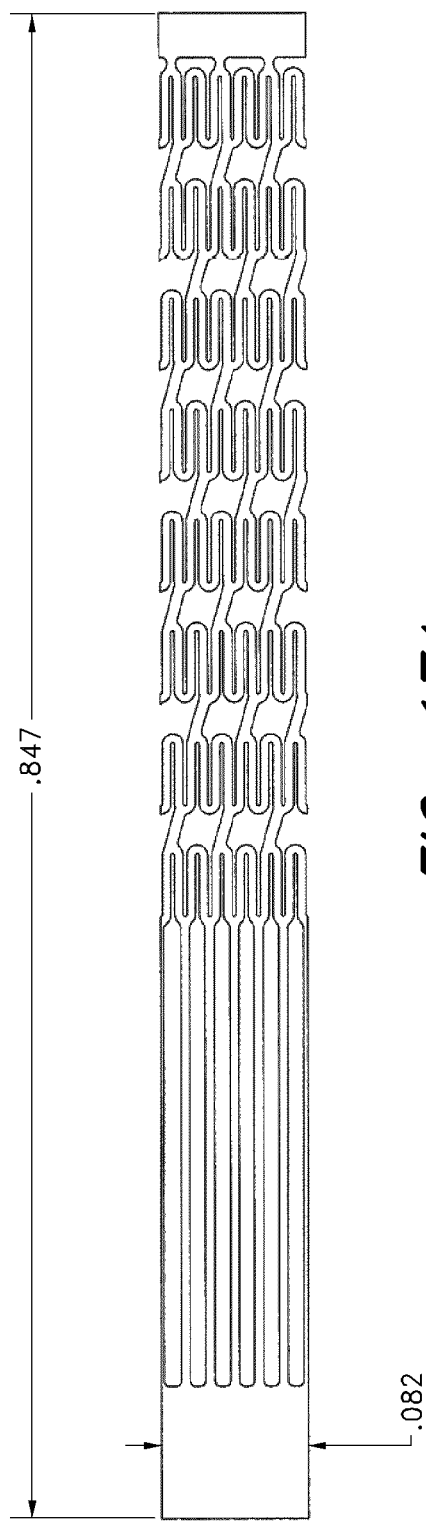
Figure 17B:
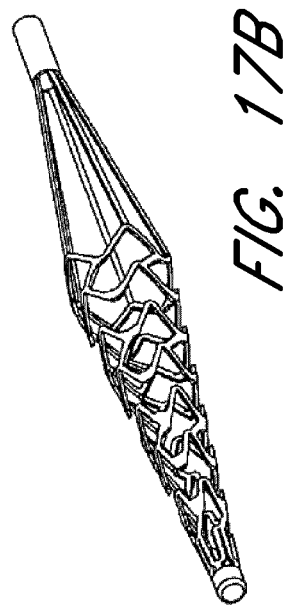
Figure 17C:
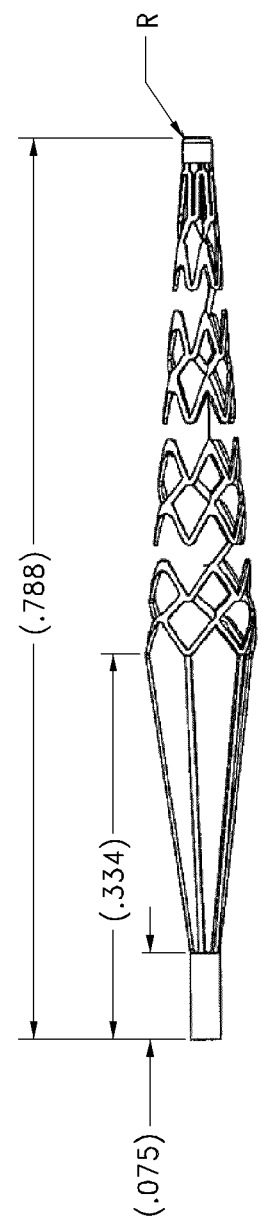
Figure 18:
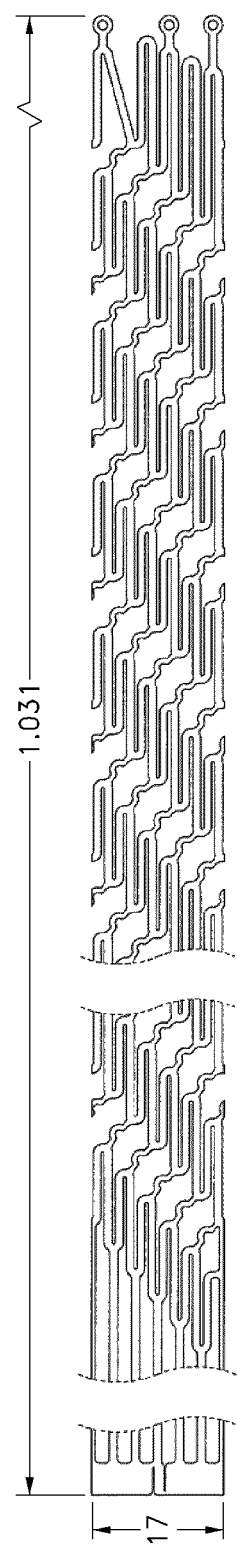
Figure 19:
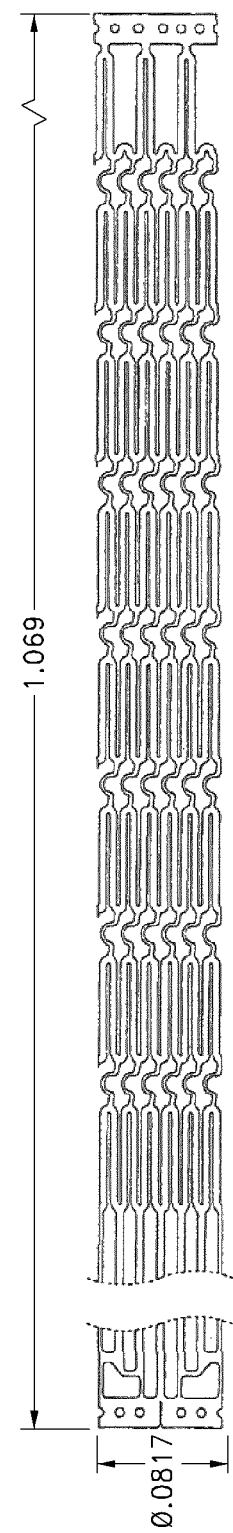
Figure 20A:
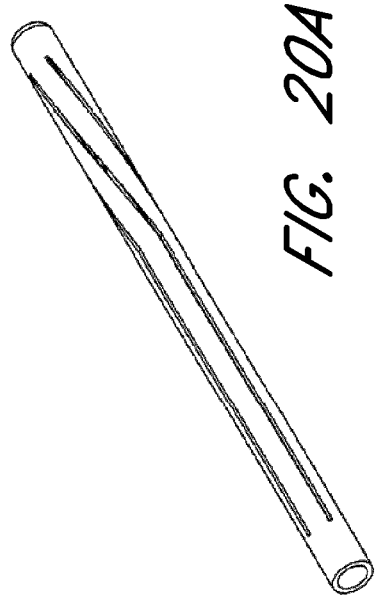
Figure 20B:
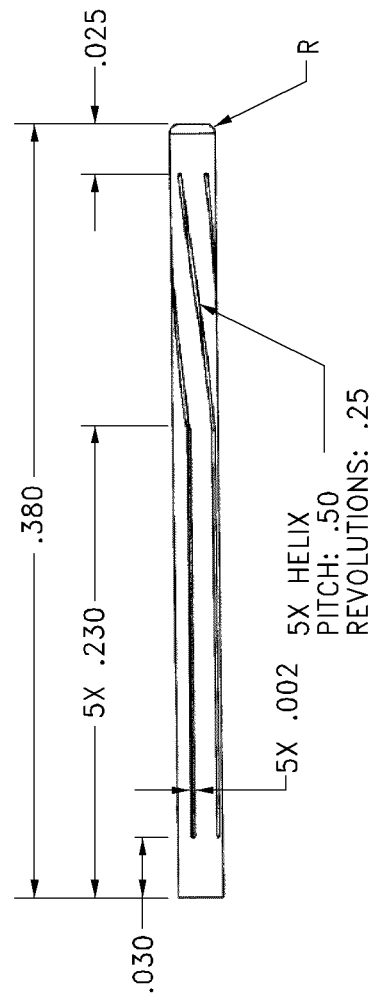
Figure 20C:

FIG. 11 illustrates a stroke device having a revascularization device 824" coupled to a distal end of an inner catheter 822". In one embodiment, a revascularization device 824" comprises one or more markers 825. The markers 825 can comprise at least one marker material selected from the group consisting essentially of platinum and gold. One or more markers can be pressed into pre-laser cut apertures designed to matingly embrace the same.

Catheter-revascularization system 800 is deployed through a patient's blood vessels. Once the user of catheter-revascularization system 800 determines that the embolus to be addressed is crossed, as known and understood well by artisans, revascularization device 824 is deployed by first positioning outer catheter 812 in a location immediately distal to the embolus.

Then, to revascularize/reperfuse the occluded blood vessel, distal catheter 820 is deployed in a location whereby revascularization device 824 expands at the location of the embolus, as illustrated by FIG. 9. The embolus is thereby compressed against the luminal wall of the blood vessel and blood flow is restored. Modular detachable segment 813 is known also, and may be swapped out, as needed, if an Rx system is used.

As discussed above and claimed below, creating a channel for flow ideally includes making a vessel at least about halfway-patent, or 50% of diameter of a vessel being open. According to other embodiments, the channel created may be a cerebral equivalent of thrombolysis in myocardial infarction TIMI 1, TIMI 2, or TIMI 3.

Restoration of blood flow may act as a natural lytic agent and many emboli may begin to dissolve. Revascularization device 824 is designed, according to embodiments, to radially filter larger pieces of the dissolving embolus and prevent them from traveling distal to the device and potentially causing occlusion in another location. Because the revascularization device provides continuous radial pressure at the location of the obstruction, as the embolus dissolves, the blood flow continues to increase.

After the embolus is lysed, revascularization device 824 is sheathed into outer catheter 812 and removed from the body. According to embodiments, larger pieces of the thrombus may be retracted with revascularization device 824 after being captured in the radial filtering process. According to embodiments, revascularization device 824 may be detachable whereby the revascularization device 824 may detach from catheter-based revascularization system 800 if it is determined that revascularization device 824 should remain in the patient. As discussed above and illustrated in the Figures, according to embodiments, catheter-based revascularization system 800 reconstrainable attachment or attachment by tether may be optionally detachable. Revascularization device detachment methods comprise mechanical, electrical hydraulic, chemical, thermal, and those other uses known to artisans.

As excerpted from U.S. Provisional No. 60/989,422, filed Nov. 20, 2007, which is incorporated herein by reference, FIGS. 12A-12F, 13A-13C, 14A-14D, 15A-15D, 16, 17A-17C, 18, 19, and 20A-20F illustrate various embodiments of cage-like structures.

As excerpted from U.S. Provisional No. 60/987,384, filed Nov. 12, 2007, which is incorporated herein by reference, FIGS. 21A, 21B, 22A, 22B, 23A, 23B, 24A, 24B, 25A, 25B, 26A-26E, 27A-27D illustrate various embodiments of rapid reperfusion devices. In one embodiment, a microcatheter having an active segment reperfuses occluded blood vessels above the junction of the subclavian artery and common carotid artery. The microcatheter is used to penetrate emboli. Once an embolus is penetrated, the active segment of the microcatheter is activated, causing it to expand radially and thereby open a channel for restored blood flow in the embolus. The blood's natural lytic action further degrades the embolus in some cases. Therapeutic agents may be administered through the microcatheter to aid in the reperfusion process. Active and passive perfusion are thus both enabled. In one embodiment, a device is disclosed comprising a distal segment having attached thereto a radially expandable active segment, a proximal segment comprising an active segment activator for radially expanding or retracting the active segment, an activation member connecting the active segment activator to the active segment. The distal segment is of a suitable diameter for use above the juncture of the subclavian artery and common carotid artery.

In one embodiment, a method is disclosed comprising providing a microcatheter having at least a distal segment, proximal segment, and active segment for use above the subclavian artery and common carotid artery, wherein the active segment is radially expandable.

In one embodiment, a catheter system for use above the juncture of the subclavian artery and common carotid artery is provided, although other uses are equally appropriate as determined by qualified medical personnel and may be introduced via a guidewire. The device operates as a standard microcatheter during introduction into a patient. The distal segment, which is remotely deployable, has attached to it an active segment that expands radially to reperfuse emboli. After reperfusion, the active segment is returned to its configuration prior to expansion and the entire microcatheter system is removed.

Figure 21A:
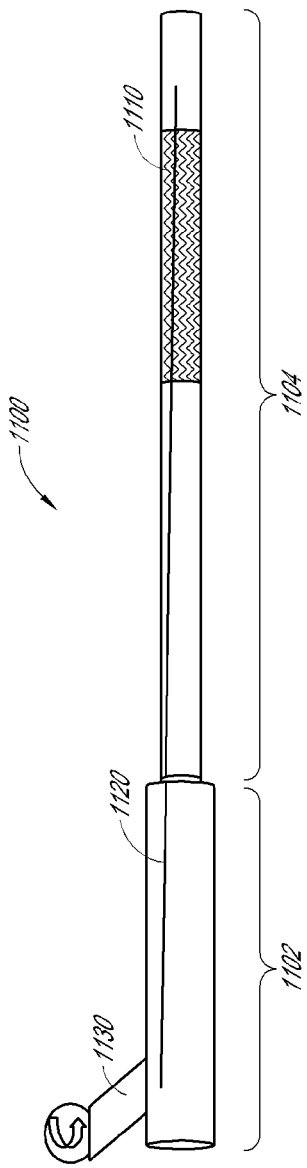
FIGS. 21A and 21B are perspective views of an embodiment of a rapid reperfusion device of the present disclosure.
Figure 21B:
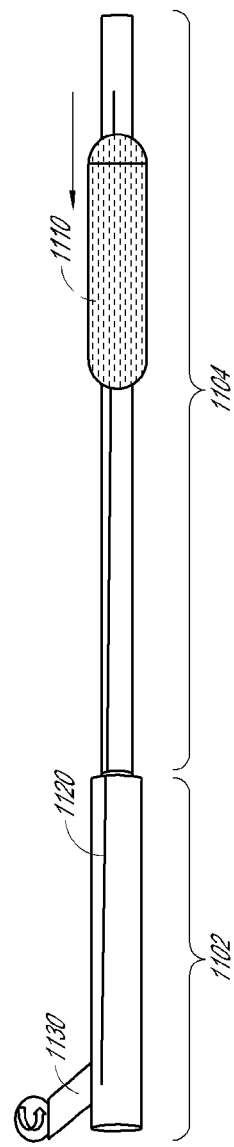

According to embodiments and as illustrated by an exemplary embodiment in FIG. 21A, there is shown microcatheter 1100. Microcatheter 1100 comprises proximal segment 1102 and distal segment 1104. Proximal segment 1102 remains outside of the patient and is used to insert and retract microcatheter 1100, as well as deploy active segment 1110 of distal segment 1104 during operation.

According to embodiments, catheter length and diameter are suitable for inserting into a human patient and capable of reaching a target embolus in the region above the subclavian and common carotid arteries. For example, according to embodiments, microcatheter 1100 is about 150 cm long; proximal segment 1102 is about 115 cm with an outer diameter of about 4 French and distal segment 1104 is about 35 cm with an outer diameter of about 2.7 French. In one embodiment, the microcatheter 1100 is 135 cm long, proximal segment 1102 is 90 cm long, and distal segment 1104 is 45 cm long. In one embodiment, the microcatheter 1100 has an inner diameter of 0.012". The inventors contemplate, according to embodiments a gradual decrease or stepwise in the outer diameter dimension as a function of the distal distance from proximal segment 1102, according to embodiments. For example, proximal segment 1102 is 4 French at the most proximal end and distal segment 1104 is 2.7 French at the most distal end. Disposed between is a segment having one or more intermediate outer diameters between 4 French and 2.7 French, such as 3.4 French and 3.0 French (see FIG. 26A). The inner diameter of microcatheter 1100 is 0.012 to 0.021 inches, according to embodiments, which allows microcatheter to be inserted along a preinserted guidewire or used to infuse therapeutic agents. According to embodiments, the performance of microcatheter is comparable to standard microcatheters and is designed to track over a guidewire through the neuro-vasculature.

According to embodiments, microcatheter 1100 is designed to follow a path of least resistance through a thrombus. Guidewire inserted through a thrombus tends to follow the path of least resistance through the softest parts of each thrombus. When microcatheter 1100 is inserted, it likewise follows this path of least resistance. As blood flow is restored, the natural lytic action further helps to break up the thrombus.

According to embodiments, active segment 1110 comprises a radially expandable woven mesh or coil. The mesh may be made from materials well known and understood by artisans, including polymers, fluoropolymers, nitinol, stainless steel, vectran, or kevlar. Other biocompatible materials that may be woven or coiled are similarly contemplated. Active segment 1110 is, according to embodiments, 5 mm to 50 mm in length when expanded and is designed to substantially return to its preexpansion configuration for removal of microcatheter after reperfusion. In one embodiment, active segment 1110 is 15 mm long.

As indicated above, active segment 1110 comprises a mesh. The mesh comprises a plurality of individual units, having a uniform size or spacing geometry or a variable size or spacing geometry. According to embodiments where the size or spacing geometry is variable, smaller size or spacing geometry is used to provide a tight mesh for expanding a channel through the thrombus. Larger size or spacing geometry units allow from blood flow through active segment 1110. In one embodiment, active segment 1110 comprises a woven polymer mesh that is heparin coated. In one embodiment, active segment 1110 has a suitable porosity to permit blood flow when expanded. In one embodiment, releasing expansion of active segment 1110 will trap thrombus in the mesh.

According to embodiments, variable cell size or spacing geometry is accomplished with points where the braid crosses over fixed filaments (PICS). Thus, the cell size or spacing geometry varies by varying the density of the braid. Where high radial force is needed to open a channel in an embolus, for example, the filaments of the mesh are denser and therefore cross each other more often, yielding small cell size or spacing geometry that leads to the application of greater radial force when the mesh expands. Where perfusion is desired, the PICS are less dense and the resulting cell size or spacing geometry is increased. Additionally, drug delivery through microcatheter will be more effective in mesh configurations having a large size or spacing geometry.

Active segment 1110 may be coated or covered with substances, such as lubricious agents or pharmacologically active agents, according to embodiments. For example, active segment 1110 may be covered with heparin or other agents that are used in clot therapy, such as those that aid in dissolving clots or mitigating vasospasms.

According to similar embodiments, therapeutic agents are deployable through the lumen of microcatheter 1100, thereby allowing users of microcatheter 1100 to determine on a case-by-case basis whether to administer an agent. Accordingly, the braid/geometry of active segment 1110 is porous to allow the agent to pass from lumen of microcatheter 1100 into the blood vessel at the site of an embolus, for example.

Activation member 1120, according to embodiments, is a wire that connects proximal segment 1102 to distal segment 1104 and allows a user of microcatheter 1100 to deploy active segment 1110. Accordingly, activation member 1120 is made from stainless steel wire or braid, composites polymers and metal braids, ribbon or wire coils. According to embodiments, activation member 1120 comprises a hollow lumen that slidably moves over a guidewire to insert microcatheter 1100.

When active segment 1110 is expanded in a vessel, the radial expansion causes a channel to be formed in a thrombus for restored blood flow past the occlusion and thereby reperfuse the vessel. Activation of active segment 1110 is accomplished by mechanical methods, such as with activation member 1120 or by using liner of microcatheter 1110. Use of the liner is accomplished by leaving the liner unfused with active segment 1110.

For example, activation member 1120 fuses to the distal-most portion of activation segment 1110. According to embodiments, activation segment 1110 is heat set into a native confirmation in an expanded state. When activation member 1120 tensions active segment 1110, its confirmation changes from an expanded state into a deliverable state. Once delivered to the site of an embolus, activation member 1120 is adjusted to allow active segment 1110 to relax and thereby expand. According to similar embodiments, active segment 1110 is heat set into a native unexpanded confirmation. Activation member 1120 is used to tension active segment 1110 when delivered to the site of an embolus, thereby expanding it.

Other activation methods include electrical, chemical, and thermal activators, as is known and understood by artisans. Hydraulic activation may be accomplished with a balloon in the interior of the catheter that is filled with a fluid, thereby expanding the balloon, which expands active segment.

According to embodiments illustrated in FIG. 22A, microcatheter is inserted into a vessel having an occlusion. As previously discussed, microcatheter is insertable along a guidewire through vessel lumen 1202, according to certain embodiments. Microcatheter 1100 penetrates embolus 1210 in vessel 1200. Active segment 1110 is positioned to coincide with the position of embolus 1210, according to techniques well known and understood by artisans. Thereafter, active segment 1110 is expanded, thereby opening a channel in thrombus 1210 and restoring blood flow, as illustrated in FIG. 22B.

Once activated, active segment 1110 allows blood to flow around microcatheter 1100 and active segment 1110 to create therapeutic benefits associated with reperfusion. For example and according to embodiments, the portions of distal segment 1104 immediately proximal and distal to active segment 1110 may have a diameter of 2.0 French to 3.0 French and have installed therein revascularization ports 1112, as shown in FIGS. 22A and 22B. Revascularization ports 1112 comprise openings in microcatheter 1100 that allow to blood flow through microcatheter 1100. Additionally, revascularization ports 1112 provide additional delivery points for therapeutic agents delivered through microcatheter 1100.

According to embodiments, a filter may be placed distal of active segment to prevent embolus pieces detached in the reperfusion process from escaping and causing distal occlusions. Accordingly, active segment is designed to capture pieces of embolus during the reperfusion processes. These pieces are captured within active segment 1110 when active segment 1110 is returned to its initial confirmation after expansion.

Figure 23A:
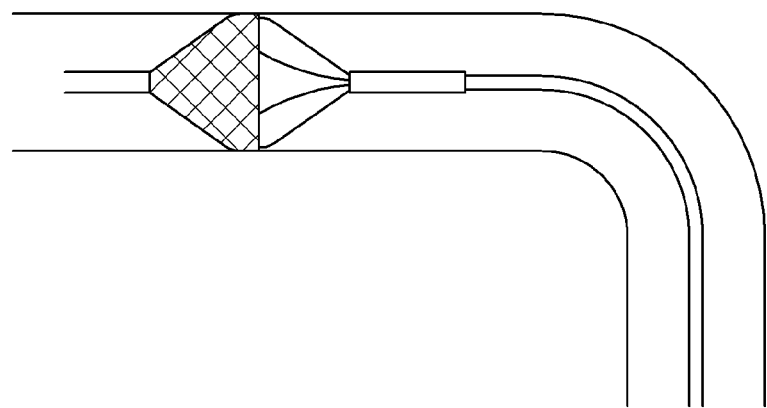
FIG. 23A is a side view of an embodiment of a rapid reperfusion device comprising an infusable microwire with an integrated filter.
Figure 23B:
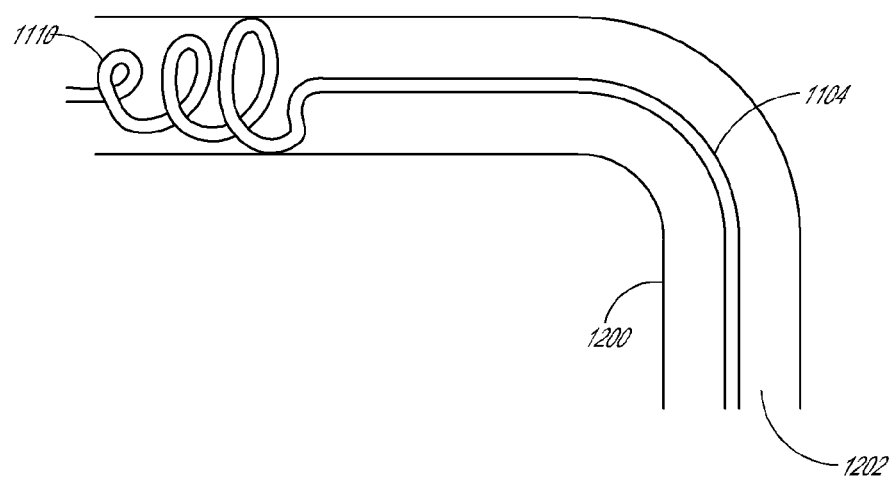
FIG. 23B is a side view of an embodiment of a rapid reperfusion device comprising an infusable coil.

In some embodiments, active segment 1110 comprises an infusable microwire with an integrated filter as illustrated in FIG. 23A. In one embodiment, the infusable microwire has a diameter of 0.014". According to embodiments and as illustrated in FIG. 23B, active segment 1110 comprises an infusable coil. In one embodiment, the infusable coil has a diameter of 0.014". Accordingly, active segment 1110 comprises a large portion of distal segment 1104, wherein microcatheter 1100 itself coils when activated to create a channel through an embolus whereby blood flow is restored.

Figure 24A:
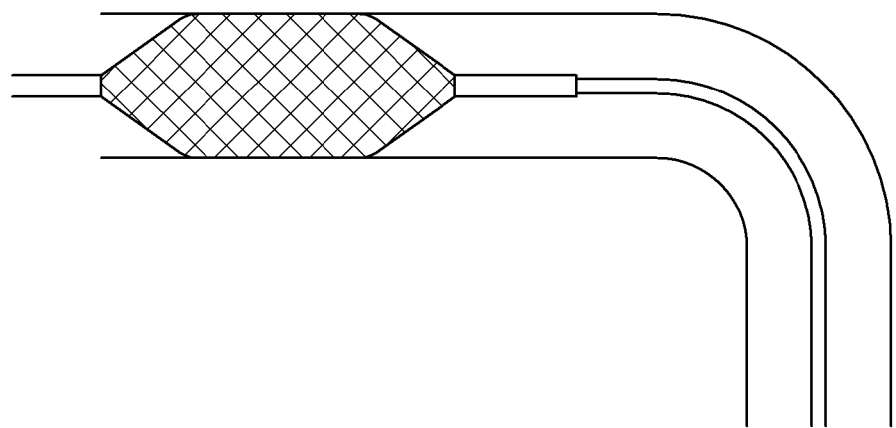
FIG. 24A is a side view of an embodiment of a rapid reperfusion device comprising an infusable temporary stent.
Figure 24B:
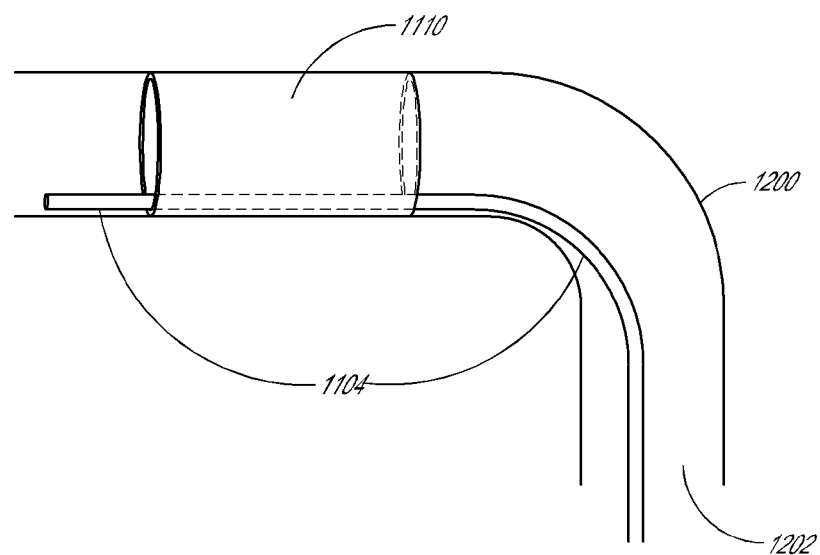
FIG. 24B is a side view of an embodiment of a rapid reperfusion device comprising an inflatable balloon.

In some embodiments, the rapid reperfusion device comprises an infusable temporary stent as illustrated in FIG. 24A. According to embodiments illustrated by FIG. 24B, an infusable balloon is connected to microcatheter 1100 and comprises active segment 1110. Inflation of the infusable balloon opens a channel through the embolus and begins the lytic process.

FIGS. 25A-27D illustrate exemplary embodiments wherein active segment 1110 comprises different configurations designed to reperfuse an occluded blood vessel. According to embodiments illustrated in FIGS. 25A and 25B, active segment 1110 comprises an expandable coiled wire. The coiled wire may be made from stainless steel wire or braid, composite metal polymers, memory shape alloys such as nitinol, etc., wherein the coil is able to stably expand and return to its original state. As illustrated in FIG. 25A, the diameter of coil is substantially the same as that of microcatheter 1100 when in a nonexpanded state. However, when expanded (as illustrated in FIG. 25B) coil expands radially according to the reperfusion principles disclosed herein. According to embodiments, revascularization ports 1112 provide for increased blood flow through the lumen of microcatheter 1100. Activation of the coil may occur as previously disclosed, for example mechanically using activation member 1120, or by electrical or heat methods, as well known and understood by artisans.

FIGS. 26A-26D illustrate an embodiment of the present disclosure wherein active segment 1110 comprises a tethered mesh. According to this embodiment, active segment 1110 comprises mesh 1110A and tethers 1110B. Mesh is the same as previously described. According to embodiments, mesh comprises an open braid or a covered braid. The covering comprises, according to embodiments, a distal protection mechanism and may be a polymer, such as polyurethane, or other biocompatible cover materials such as ePTFE or related thin film. Tethers 1110B serve to provide structure for mesh 1110A, while providing large openings whereby blood may freely flow from the proximal to distal end of active segment 1110. Those skilled in the art will readily understand that materials for tethers and mesh may be the same, different, or interchangeable, as needed. FIG. 26E illustrates an embodiment of an active segment comprising an open braid or covered braid configured to be connected to the microcatheter via tethers or an open braid at both the proximal and distal end, thereby forming an open proximal end and an open distal end.

Figure 26B:
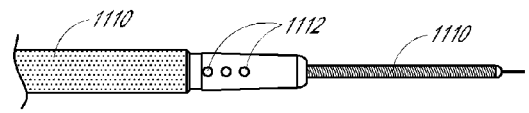
FIGS. 26A-26D are perspective views of an embodiment of a rapid perfusion device wherein the active segment comprises a covered or uncovered mesh connected to the microcatheter via tethers.
Figure 26A:
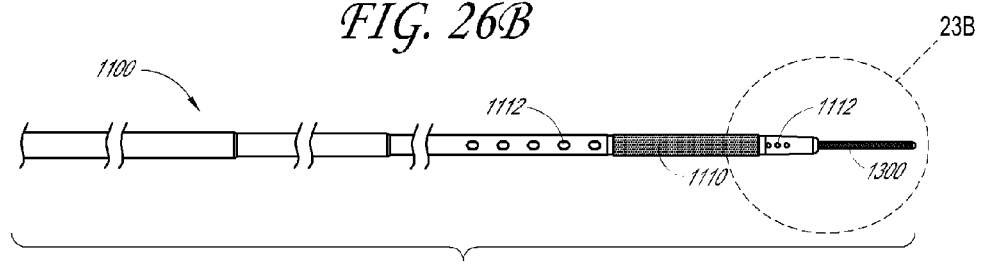
Figure 26D:
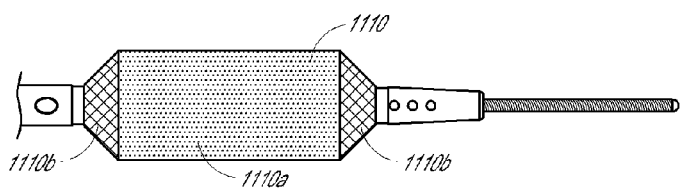
Figure 26C:
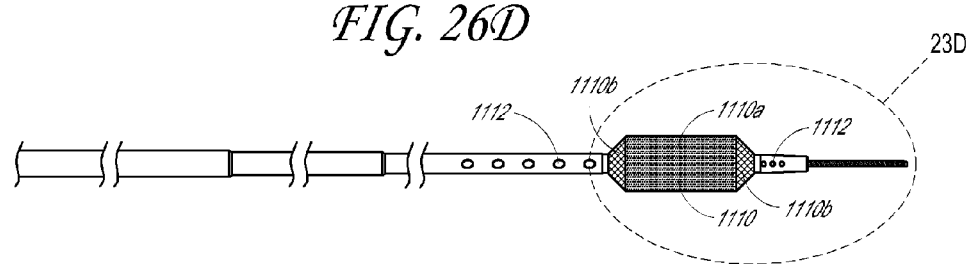
Figure 26E:
FIG. 26E is a side view of an embodiment of an active segment comprising an open braid or covered braid configured to be connected to the microcatheter via tethers or an open braid on both the proximal and distal ends.

As shown in FIGS. 26A and 26B, microcatheter 1100 is inserted along guidewire 1300. In some embodiments, guidewire 1300 is compatible with 0.010" and 0.014". Active segment is initially in a non-expanded configuration. FIGS. 26C and 26D illustrate embodiments of active segment 1110 when extended. In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

According to embodiments illustrated in FIGS. 27A-27D, active segment 1110 comprises a wire mesh having variable spacing between the wires. FIGS. 27A and 27B illustrate active segment 1110 in a non-expanded configuration. FIGS. 27C and 27D illustrate active segment 1110 in an expanded position, as disclosed herein. In some embodiments, guidewire 1300 is compatible with 0.010" and 0.014". In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

While the apparatuses and methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would hare literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising" are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An improved system for bridging aneurysms in neurovasculature, the system comprising:
   a first microcatheter for accessing neurovascular vessels over a guidewire;
   a variable stiffness delivery tube comprising a proximal section and a distal section,
   wherein said distal section has a decreased stiffness and a greater flexibility as compared to the proximal section to allow tracking through tortuous anatomy of the neurovasculature,
   wherein said variable stiffness delivery tube comprises an internal lumen configured to receive a guidewire, said guidewire providing trackability, maintained access and vessel support; and
   a tethered cage-like structure eccentrically coupled to said delivery tube via a plurality of tethers such that the tethered cage-like structure is temporary and configured for removal from a patient's body,
   wherein said cage-like structure has an open proximal end, an open distal end, and a tapering portion, the tapering portion located between the plurality of tethers and the open distal end, the tapering portion tapering, in absence of external forces, between a proximal end of the tapering portion and the open distal end such that said cage-like structure has a first circumference at the proximal end of the tapering portion and a second circumference, smaller than the first circumference, at the open distal end,
   wherein said cage-like structure comprises a plurality of struts and a plurality of openings formed between the struts to provide vessel support without obstructing blood flow,
   wherein said cage-like structure can be delivered to a target site local to an aneurysm and positioned to bridge the neck of the aneurysm, thereby covering the aneurysm to reconstruct a vessel wall; and
   whereby a second microcatheter can be threaded through one or more open cells of the cage-like structure for delivery of supplemental therapy to the aneurysm while maintaining revascularization.

2. The system of claim 1, the supplemental therapy being deployment of vasa-occlusive coils.

3. The system of claim 1, wherein the aneurysm is reperfused through the origin of the aneurysm.

4. The system of claim 1, wherein the tethered cage-like structure is expandable and reconstrainable.

5. The system of claim 1, wherein the tethered cage-like structure is self-expandable.

6. The system of claim 1, wherein the aneurysm comprises a wide-neck aneurysm having a dome to neck ratio of less than 2:1.

7. The system of claim 1, wherein said delivery tube comprises a hypotube.

8. The system of claim 1, wherein said cage-like structure comprises a super-elastic material.

9. The system of claim 8, wherein said cage-like structure comprises Nitinol.

10. The system of claim 1, wherein said cage-like structure is coupled to the delivery tube by soldering.

11. The system of claim 1, wherein said cage-like structure is coupled to the delivery tube by welding.

12. The system of claim 1, wherein said cage-like structure is coupled to the delivery tube by press-fitting.

13. The system of claim 1, wherein said cage-like structure has an aspect ratio of 0.05 (thickness/width) or less.

14. The system of claim 1, wherein said cage-like structure is configured to be recaptured into the first microcatheter and repositioned.

15. The system of claim 1, wherein the aneurysm comprises a wide-neck aneurysm having a neck greater than 4 mm.

16. A temporary aneurysm neck bridge device for placement across a neck of an aneurysm, the temporary aneurysm neck bridge device comprising:
   a delivery device;
   a tethered cage-like structure eccentrically coupled to a distal end of the delivery device by a plurality of tether lines such that the tethered cage-like structure is configured for removal from a patient's body, the tethered cage-like structure having an open strut design that is expandable from a non-expanded configuration to an expanded configuration upon being unsheathed from a microcatheter, said tethered cage-like structure having an open proximal end, an open distal end, and a tapering portion, the tapering portion located between the plurality of tether lines and the open distal end, the tapering portion tapering, in absence of external forces, between a proximal end of the tapering portion and the open distal end such that said tethered cage-like structure has a first circumference at the proximal end of the tapering portion and a second circumference, smaller than the first circumference, at the open distal end of the tapering portion, said tethered cage-like structure being configured to be delivered within a blood vessel to a neck of an aneurysm while housed within the microcatheter in the non-expanded configuration; and
   radiopaque markers configured to allow tracking of the cage-like structure,
   wherein, in use, said tethered cage-like structure is configured to transition from said non-expanded configuration to said expanded configuration at a location such that the tethered cage-like structure bridges the neck of the aneurysm upon retraction of the microcatheter within which the tethered cage-like structure is housed.

17. The device of claim 16, the tethered cage-like structure further comprised of variable cell sizes.

18. The device of claim 16, the radiopaque markers further comprised of at least one of platinum and gold pegs pressed into pre-laser cut holes.

19. The device of claim 16, wherein the delivery device is a delivery tube.

20. The device of claim 19, wherein the delivery tube is a variable stiffness tube that is configured to navigate through tortuous anatomy of the cerebral vasculature to distal cerebral arteries.

21. The device of claim 20, wherein a distal portion of the delivery tube has greater flexibility than a proximal portion of the delivery tube.

22. The device of claim 16, wherein the delivery device is a delivery wire.

* * * * *